(12) United States Patent
Dinh

(10) Patent No.: US 11,937,834 B2
(45) Date of Patent: Mar. 26, 2024

(54) SYSTEMS, DEVICES, AND METHODS FOR TREATING VASCULAR OCCLUSIONS

(71) Applicant: Inari Medical, Inc., Irvine, CA (US)

(72) Inventor: James Quang Dinh, Irvine, CA (US)

(73) Assignee: Inari Medical, Inc., Irvine, CA (US)

( * ) Notice: Subject to any disclaimer, the term of this patent is extended or adjusted under 35 U.S.C. 154(b) by 0 days.

(21) Appl. No.: 18/351,326

(22) Filed: Jul. 12, 2023

(65) Prior Publication Data

US 2023/0355256 A1    Nov. 9, 2023

Related U.S. Application Data

(63) Continuation of application No. 17/072,909, filed on Oct. 16, 2020.

(60) Provisional application No. 62/916,044, filed on Oct. 16, 2019.

(51) Int. Cl.
*A61B 17/22* (2006.01)
*A61B 17/00* (2006.01)

(52) U.S. Cl.
CPC .... *A61B 17/22* (2013.01); *A61B 2017/00867* (2013.01); *A61B 2017/22038* (2013.01); *A61B 2017/22079* (2013.01)

(58) Field of Classification Search
CPC .......... A61B 17/22; A61B 2017/00867; A61B 2017/22038; A61B 2017/22079; A61B 17/221
See application file for complete search history.

(56) References Cited

U.S. PATENT DOCUMENTS

| | | | |
|---|---|---|---|
| 1,101,890 | A | 6/1914 | Tunstead |
| 2,784,717 | A | 3/1957 | Thompson |
| 2,846,179 | A | 8/1958 | Monckton |
| 2,955,592 | A | 10/1960 | Maclean |
| 3,088,363 | A | 5/1963 | Sparks |
| 3,197,173 | A | 7/1965 | Taubenheim |
| 3,416,531 | A | 12/1968 | Edwards |

(Continued)

FOREIGN PATENT DOCUMENTS

| | | |
|---|---|---|
| AU | 2015210338 | 8/2015 |
| CN | 102186427 | 9/2011 |

(Continued)

OTHER PUBLICATIONS

Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.

(Continued)

*Primary Examiner* — Julian W Woo
(74) *Attorney, Agent, or Firm* — Perkins Coie LLP

(57) ABSTRACT

Systems and methods for the intravascular treatment of clot material within a blood vessel of a human patient. A device in accordance with embodiments of the present technology can include, for example, a plurality of interconnected struts forming a unitary structure having a proximal portion and a distal portion. The struts can form a plurality of first cells in the proximal portion and a plurality of second cells, smaller than the first cells, in the distal portion. The device can be pulled against clot material within a blood vessel to engage, disrupt, and/or capture the clot material.

22 Claims, 12 Drawing Sheets

(56) References Cited

U.S. PATENT DOCUMENTS

| | | |
|---|---|---|
| 3,435,826 A | 4/1969 | Fogarty |
| 3,438,607 A | 4/1969 | Williams et al. |
| 3,515,137 A | 6/1970 | Santomieri |
| 3,675,657 A | 7/1972 | Gauthier |
| 3,860,006 A | 1/1975 | Patel |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,401,107 A | 8/1983 | Harber et al. |
| 4,469,100 A | 9/1984 | Hardwick |
| 4,523,738 A | 6/1985 | Raftis et al. |
| 4,551,862 A | 11/1985 | Haber |
| 4,604,094 A | 8/1986 | Shook |
| 4,611,594 A | 9/1986 | Grayhack et al. |
| 4,634,421 A | 1/1987 | Hegemann |
| 4,643,184 A | 2/1987 | Mobin-Uddin |
| 4,646,736 A | 3/1987 | Auth et al. |
| 4,650,466 A | 3/1987 | Luther |
| 4,776,337 A | 10/1988 | Palmaz |
| 4,790,812 A | 12/1988 | Hawkins, Jr. et al. |
| 4,863,440 A | 9/1989 | Chin et al. |
| 4,870,953 A | 10/1989 | DonMichael et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 4,981,478 A | 1/1991 | Evard et al. |
| 5,030,201 A | 7/1991 | Palestrant |
| 5,059,178 A | 10/1991 | Ya |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,158,533 A | 10/1992 | Strauss et al. |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,197,485 A | 3/1993 | Grooters |
| 5,234,403 A | 8/1993 | Yoda et al. |
| 5,242,461 A | 9/1993 | Kortenbach et al. |
| 5,244,619 A | 9/1993 | Burnham |
| 5,329,923 A | 7/1994 | Lundquist |
| 5,360,417 A | 11/1994 | Gravener et al. |
| 5,364,345 A | 11/1994 | Lowery et al. |
| 5,376,101 A | 12/1994 | Green et al. |
| 5,383,887 A | 1/1995 | Nadal |
| 5,389,100 A | 2/1995 | Bacich et al. |
| 5,391,152 A | 2/1995 | Patterson et al. |
| 5,419,774 A | 5/1995 | Willard et al. |
| 5,421,824 A | 6/1995 | Clement et al. |
| 5,443,443 A | 8/1995 | Shiber |
| 5,456,667 A | 10/1995 | Ham et al. |
| 5,476,450 A | 12/1995 | Ruggio |
| 5,484,418 A | 1/1996 | Quiachon et al. |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,639,276 A | 6/1997 | Weinstock et al. |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,873,866 A | 2/1999 | Kondo et al. |
| 5,873,882 A | 2/1999 | Straub et al. |
| 5,876,414 A | 3/1999 | Straub |
| 5,895,406 A | 4/1999 | Gray et al. |
| 5,908,435 A | 6/1999 | Samuels |
| 5,911,710 A | 6/1999 | Barry et al. |
| 5,911,733 A | 6/1999 | Parodi |
| 5,911,754 A | 6/1999 | Kanesaka et al. |
| 5,941,869 A | 8/1999 | Patterson et al. |
| 5,947,985 A | 9/1999 | Imram |
| 5,954,737 A | 9/1999 | Lee |
| 5,971,938 A | 10/1999 | Hart et al. |
| 5,971,958 A | 10/1999 | Zhang |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,017,335 A | 1/2000 | Burnham |
| 6,030,397 A | 2/2000 | Moneti et al. |
| 6,059,814 A | 5/2000 | Ladd |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |
| 6,146,403 A | 11/2000 | St. Germain |
| 6,152,144 A | 11/2000 | Lesh et al. |
| 6,152,946 A | 11/2000 | Broome et al. |
| 6,156,055 A | 12/2000 | Ravenscroft |
| 6,159,230 A * | 12/2000 | Samuels .......... A61B 17/22032 606/200 |
| 6,165,196 A | 12/2000 | Stack et al. |
| 6,168,579 B1 | 1/2001 | Tsugita |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,564,828 B1 | 5/2003 | Ishida |
| 6,569,181 B1 | 5/2003 | Burns |
| 6,575,995 B1 | 6/2003 | Huter et al. |
| 6,589,263 B1 | 7/2003 | Hopkins et al. |
| 6,589,264 B1 | 7/2003 | Barbut et al. |
| 6,596,011 B2 | 7/2003 | Johnson et al. |

(56) References Cited

U.S. PATENT DOCUMENTS

| | | |
|---|---|---|
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,222 B1 | 11/2003 | Parodi et al. |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,790,204 B2 | 9/2004 | Zadno-azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,939,361 B1 | 9/2005 | Kleshinski |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,036,707 B2 | 5/2006 | Aota et al. |
| 7,041,084 B2 | 5/2006 | Fotjik |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,179,273 B1 | 2/2007 | Palmer et al. |
| 7,223,253 B2 * | 5/2007 | Hogendijk ............ A61B 17/22 604/9 |
| 7,232,432 B2 | 6/2007 | Fulton, III et al. |
| 7,244,243 B2 | 7/2007 | Lary |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,481,805 B2 | 1/2009 | Magnusson |
| 7,534,234 B2 | 5/2009 | Fotjik |
| 7,578,830 B2 | 8/2009 | Kusleika et al. |
| 7,621,870 B2 | 11/2009 | Berrada et al. |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,815,608 B2 | 10/2010 | Schafersman et al. |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,021,351 B2 | 9/2011 | Boldenow et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,829 B2 | 2/2012 | Carrison et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,512,352 B2 | 8/2013 | Martin |
| 8,523,897 B2 | 9/2013 | van der Burg et al. |
| 8,535,283 B2 | 9/2013 | Heaton et al. |
| 8,535,334 B2 | 9/2013 | Martin |
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,771,289 B2 | 7/2014 | Mohiuddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,205 B2 | 10/2014 | Brady et al. |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,028,401 B1 | 5/2015 | Bacich et al. |

(56) References Cited

U.S. PATENT DOCUMENTS

| | | |
|---|---|---|
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van der Burg et al. |
| 9,173,668 B2 | 11/2015 | Ulm, III |
| 9,186,487 B2 | 11/2015 | Dubrul et al. |
| 9,204,887 B2 | 12/2015 | Cully et al. |
| 9,216,277 B2 | 12/2015 | Myers |
| 9,241,669 B2 | 1/2016 | Pugh et al. |
| 9,358,037 B2 | 1/2016 | Farhangnia et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,526,864 B2 | 12/2016 | Quick |
| 9,526,865 B2 | 12/2016 | Quick |
| 9,532,792 B2 | 1/2017 | Galdonik et al. |
| 9,566,073 B2 | 2/2017 | Kassab et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,844,386 B2 | 12/2017 | Nguyen et al. |
| 9,844,387 B2 | 12/2017 | Marchand et al. |
| 9,848,975 B2 | 12/2017 | Hauser |
| 9,849,014 B2 | 12/2017 | Kusleika |
| 9,884,387 B2 | 2/2018 | Plha |
| 9,962,178 B2 | 5/2018 | Greenhalgh et al. |
| 9,980,813 B2 | 5/2018 | Eller |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,045,790 B2 | 8/2018 | Cox et al. |
| 10,058,339 B2 | 8/2018 | Galdonik et al. |
| 10,098,651 B2 | 10/2018 | Marchand et al. |
| 10,130,385 B2 | 11/2018 | Farhangnia et al. |
| 10,183,159 B2 | 1/2019 | Nobles et al. |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molaei et al. |
| 10,384,034 B2 | 8/2019 | Carrison et al. |
| 10,456,555 B2 | 10/2019 | Carrison et al. |
| 10,478,535 B2 | 11/2019 | Ogle |
| 10,485,952 B2 | 11/2019 | Carrison et al. |
| 10,524,811 B2 | 1/2020 | Marchand et al. |
| 10,531,883 B1 | 1/2020 | Deville et al. |
| 10,588,655 B2 | 3/2020 | Rosenbluth et al. |
| 10,648,268 B2 | 5/2020 | Jaffrey et al. |
| 10,695,159 B2 | 6/2020 | Hauser |
| 10,709,471 B2 | 7/2020 | Rosenbluth et al. |
| 10,772,636 B2 | 9/2020 | Kassab et al. |
| 10,799,331 B2 | 10/2020 | Hauser |
| 10,912,577 B2 | 2/2021 | Marchand et al. |
| 10,926,060 B2 | 2/2021 | Stern et al. |
| 10,953,195 B2 | 3/2021 | Jalgaonkar et al. |
| 10,960,114 B2 | 3/2021 | Goisis |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,065,019 B1 | 7/2021 | Chou et al. |
| 11,147,571 B2 | 10/2021 | Cox et al. |
| 11,154,314 B2 | 10/2021 | Quick |
| 11,166,703 B2 | 11/2021 | Kassab et al. |
| 11,185,664 B2 | 11/2021 | Carrison et al. |
| 11,224,450 B2 | 1/2022 | Chou et al. |
| 11,224,721 B2 | 1/2022 | Carrison et al. |
| 11,259,821 B2 | 3/2022 | Buck et al. |
| 11,305,094 B2 | 4/2022 | Carrison et al. |
| 11,383,064 B2 | 7/2022 | Carrison et al. |
| 11,395,903 B2 | 7/2022 | Carrison et al. |
| 11,406,801 B2 | 8/2022 | Fojtik et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,529,158 B2 | 12/2022 | Hauser |
| 11,554,005 B2 | 1/2023 | Merritt et al. |
| 11,559,382 B2 | 1/2023 | Merritt et al. |
| 11,576,691 B2 | 2/2023 | Chou et al. |
| 11,596,768 B2 | 3/2023 | Stern et al. |
| 11,642,209 B2 | 5/2023 | Merritt et al. |
| 11,648,028 B2 | 5/2023 | Rosenbluth et al. |
| 11,697,011 B2 | 7/2023 | Merritt et al. |
| 11,697,012 B2 | 7/2023 | Merritt et al. |
| 11,744,691 B2 | 9/2023 | Merritt et al. |
| 11,806,033 B2 | 11/2023 | Marchand et al. |
| 11,832,837 B2 | 12/2023 | Hauser |
| 11,832,838 B2 | 12/2023 | Hauser |
| 11,833,023 B2 | 12/2023 | Merritt et al. |
| 11,839,393 B2 | 12/2023 | Hauser |
| 2001/0004699 A1 | 6/2001 | Gittings et al. |
| 2001/0031981 A1 | 10/2001 | Evans et al. |
| 2001/0041909 A1 | 11/2001 | Tsugita et al. |
| 2001/0049486 A1 | 12/2001 | Evans et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0023263 A1 | 1/2003 | Krolik et al. |
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191516 A1 | 10/2003 | Weldon et al. |
| 2003/0208224 A1 | 11/2003 | Broome |
| 2003/0216774 A1 | 11/2003 | Larson |

(56) References Cited

U.S. PATENT DOCUMENTS

| | | |
|---|---|---|
| 2004/0019310 A1 | 1/2004 | Hogendijk |
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0089533 A1 | 4/2006 | Ziegler et al. |
| 2006/0100662 A1 | 5/2006 | Daniel et al. |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber, III et al. |
| 2008/0300466 A1 | 12/2008 | Gresham |
| 2008/0312681 A1 | 12/2008 | Ansel et al. |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desai |
| 2010/0190156 A1 | 7/2010 | Van Wordragen et al. |
| 2010/0204712 A1 | 8/2010 | Mallaby |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0101480 A1 | 4/2012 | Ingle et al. |
| 2012/0101510 A1 | 4/2012 | Lenker et al. |
| 2012/0109109 A1 | 5/2012 | Kaji |
| 2012/0138832 A1 | 6/2012 | Townsend |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |

(56) References Cited

U.S. PATENT DOCUMENTS

| | | |
|---|---|---|
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0184703 A1 | 7/2013 | Shireman et al. |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0155830 A1 | 6/2014 | Bonnette et al. |
| 2014/0155980 A1 | 6/2014 | Turjman |
| 2014/0180055 A1 | 6/2014 | Glynn et al. |
| 2014/0180397 A1 | 6/2014 | Gerberding et al. |
| 2014/0155908 A1 | 7/2014 | Rosenbluth et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth et al. |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0305756 A1 | 10/2015 | Rosenbluth |
| 2015/0305859 A1 | 10/2015 | Eller |
| 2015/0352325 A1 | 12/2015 | Quick |
| 2015/0360001 A1 | 12/2015 | Quick |
| 2015/0374391 A1 | 12/2015 | Quick |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0135829 A1 | 5/2016 | Holochwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0008014 A1 | 8/2016 | Rosenbluth |
| 2016/0220741 A1 | 8/2016 | Garrison et al. |
| 2016/0228134 A1 | 8/2016 | Martin et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112514 A1 | 4/2017 | Marchand et al. |
| 2017/0113005 A1 | 4/2017 | Linder et al. |
| 2017/0143359 A1 | 5/2017 | Nguyen et al. |
| 2017/0143938 A1 | 5/2017 | Ogle et al. |
| 2017/0172591 A1 | 6/2017 | Ulm, III |
| 2017/0112513 A1 | 7/2017 | Marchand et al. |
| 2017/0189041 A1 | 7/2017 | Cox et al. |
| 2017/0196576 A1 | 7/2017 | Long et al. |
| 2017/0233908 A1 | 8/2017 | Kroczynski et al. |
| 2017/0252057 A1 | 9/2017 | Bonnette et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0092652 A1 | 4/2018 | Marchand et al. |
| 2018/0104404 A1 | 4/2018 | Ngo-Chu |

(56) References Cited

U.S. PATENT DOCUMENTS

| | | |
|---|---|---|
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0296240 A1 | 10/2018 | Rosenbluth et al. |
| 2018/0344339 A1 | 12/2018 | Cox et al. |
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2020/0022711 A1 | 1/2020 | Look et al. |
| 2020/0046368 A1 | 2/2020 | Merritt et al. |
| 2020/0046940 A1 | 2/2020 | Carrison et al. |
| 2020/0113412 A1 | 4/2020 | Jensen |
| 2020/0121334 A1 | 4/2020 | Galdonik et al. |
| 2021/0022843 A1 | 1/2021 | Hauser |
| 2021/0038385 A1 | 2/2021 | Popp et al. |
| 2021/0113224 A1 | 4/2021 | Dinh |
| 2021/0137667 A1 | 5/2021 | Sonnette et al. |
| 2021/0138194 A1 | 5/2021 | Carrison et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0290925 A1 | 9/2021 | Merritt et al. |
| 2021/0315598 A1 | 10/2021 | Buck et al. |
| 2021/0316127 A1 | 10/2021 | Buck et al. |
| 2021/0330344 A1 | 10/2021 | Rosenbluth et al. |
| 2021/0378694 A1 | 12/2021 | Thress et al. |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0022898 A1 | 1/2022 | Cox et al. |
| 2022/0033888 A1 | 2/2022 | Schnall-Levin et al. |
| 2022/0039815 A1 | 2/2022 | Thress et al. |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0211992 A1 | 7/2022 | Merritt et al. |
| 2022/0240959 A1 | 8/2022 | Quick |
| 2022/0346800 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2023/0046775 A1 | 2/2023 | Quick |
| 2023/0059721 A1 | 2/2023 | Chou et al. |
| 2023/0062809 A1 | 3/2023 | Merritt et al. |
| 2023/0070120 A1 | 3/2023 | Cox et al. |
| 2023/0122587 A1 | 4/2023 | Chou et al. |
| 2023/0200970 A1 | 6/2023 | Merritt et al. |
| 2023/0218310 A1 | 7/2023 | Scheinblum et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0270991 A1 | 8/2023 | Merritt et al. |
| 2023/0310137 A1 | 10/2023 | Merritt et al. |
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |
| 2023/0338131 A1 | 10/2023 | Merritt et al. |
| 2023/0355259 A1 | 11/2023 | Marchand et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0389932 A1 | 12/2023 | Ozenne et al. |
| 2023/0390045 A1 | 12/2023 | Merritt et al. |

FOREIGN PATENT DOCUMENTS

| | | |
|---|---|---|
| CN | 103764049 | 4/2014 |
| CN | 103932756 | 7/2014 |
| CN | 104068910 | 10/2014 |
| CN | 106178227 | 12/2016 |
| CN | 108348319 | 7/2018 |
| CN | 110652645 | 1/2020 |
| CN | 111281482 | 6/2020 |
| DE | 102017004383 | 7/2018 |
| EP | 1254634 | 11/2002 |
| EP | 1867290 | 2/2013 |
| EP | 2942624 | 11/2015 |
| EP | 3583972 | 12/2019 |
| EP | 3589348 | 1/2020 |
| EP | 3620204 | 3/2020 |
| EP | 3013404 | 4/2020 |
| EP | 4137070 | 2/2023 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2004097807 | 4/2004 |
| JP | 2005-095242 | 6/2005 |
| JP | 2005230132 | 9/2005 |
| JP | 2005323702 | 11/2005 |
| JP | 2006094876 | 4/2006 |
| JP | 2011526820 | 1/2010 |
| WO | WO1997017889 | 5/1997 |
| WO | WO9833443 | 8/1998 |
| WO | WO9838920 | 9/1998 |
| WO | WO9839053 | 9/1998 |
| WO | WO9851237 | 11/1998 |
| WO | WO1999044542 | 9/1999 |
| WO | WO0032118 | 6/2000 |
| WO | WO2000053120 | 9/2000 |
| WO | WO0202162 | 1/2002 |
| WO | WO03015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2009082513 | 7/2009 |
| WO | WO2009086482 | 7/2009 |
| WO | WO2009155571 | 12/2009 |
| WO | WO2010002549 | 1/2010 |
| WO | WO2010010545 | 1/2010 |
| WO | WO2010023671 | 3/2010 |

(56) References Cited

FOREIGN PATENT DOCUMENTS

| | | |
|---|---|---|
| WO | WO2010049121 | 5/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2017024258 | 2/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2023137341 | 7/2023 |
| WO | WO2023147353 | 8/2023 |
| WO | WO2023154612 | 8/2023 |
| WO | WO2023192925 | 10/2023 |
| WO | WO2023215779 | 11/2023 |

OTHER PUBLICATIONS

Gupta, S. et al., "Acute Pulmonary Embolism Advances in Treatment", JAPI, Association of Physicians India, Mar. 2008, vol. 56, 185-191.

International Search Report and Written Opinion for International App. No. PCT/US13/61470, dated Jan. 17, 2014, 7 pages.

International Search Report and Written Opinion for International App. No. PCT/US2014/046567, dated Nov. 3, 2014, 13 pages.

International Search Report and Written Opinion for International App. No. PCT/US2014/061645, dated Jan. 23, 2015, 15 pages.

International Search Report for International App. No. PCT/US13/71101, dated Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", Cardiology Rounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology; 2011: 34:106-113.

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.

Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radiol 16:7-10 1993 4 pgs.

Schmitz-Rode et al., "Temporary Pulmonary Stent Placement as Emergency Treatment of Pulmonary Embolism," Journal of the American College of Cardiology, vol. 48, No. 4, 2006 (5 pgs.).

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.

Spiotta, A et al., "Evolution of thrombectomy approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism", The New England Journal of Medicine, Mar. 6, 2008:358:2037-52.

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.

Truong et al., "Mechanical Thrombectomy of Iliocaval Thrombosis Using a Protective Expandable Sheath," Cardiovasc Intervent Radiol27-254-258, 2004, 5 pgs.

Turk et al., "ADAPT FAST study: a direct aspiration first pass technique for acute stroke thrombectomy." J NeuroIntervent Surg, vol. 6, 2014, 6 pages.

Uflacker, R., "Interventional Therapy for Pulmonary Embolism", Journal of Vascular and Interventional Radiology, Feb. 2001: 12:147-164.

Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.

International Search Report and Written Opinion for International App. No. PCT/US2015/034987 filed Jun. 9, 2015, Applicant: Inceptus Medical, LLC, dated Sep. 17, 2015, 12 pages.

(56) References Cited

OTHER PUBLICATIONS

International Search Report and Written Opinion for International App. No. PCT/US2016/067628 filed Dec. 19, 2016, Applicant: Inari Medical, Inc., dated Apr. 10, 2017, 11 pages.
Goldhaber, S. et al. "Percutaneous Mechanical Thrombectomy for Acute Pulmonary Embolism—A Double-Edged Sword," American College of CHEST Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc., dated Sep. 15, 2017, 19 pages.
International Search Report and Written Opinion for International App. No. PCT/US2016/058536, Date of Filing: Oct. 24, 2016, Applicant: Inari Medical, Inc., dated Mar. 13, 2017, 14 pages.
International Search Report and Written Opinion for International App. No. PCT/US2018/048786, Date of Filing: Aug. 30, 2018, Applicant: Inari Medical, Inc., dated Dec. 13, 2018, 12 pages.
International Search Report and Written Opinion for International App. No. PCT/US2018/055780, Date of Filing: Oct. 13, 2018, Applicant: Inceptus Medical LLC., dated Jan. 22, 2019, 8 pages.
International Search Report and Written Opinion for International App. No. PCT/US2019/045794, Date of Filing: Aug. 8, 2019, Applicant: Inari Medical, Inc., dated Nov. 1, 2019, 17 pages.
International Search Report and Written Opinion for International App. No. PCT/US2020/056067, Date of Filing: Oct. 16, 2020; Applicant: Inari Medical, Inc., dated Jan. 22, 2021, 8 pages.
International Search Report and Written Opinion for International App. No. PCT/US2020/055645, Date of Filing: Dec. 17, 2020; Applicant: Inari Medical, Inc., dated Apr. 14, 2021, 12 pages.
Vorwerk, D. MD, et al., "Use of a Temporary Caval Filter to Assist Percutaneous Iliocaval Thrombectomy: Experimental Results." SCVIR, 1995, 4 pages.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information);retrieved from the internet: http://www.bostonscientific.com/en-US/products/thrombectomy-systems/fetch2-aspiration-catheter.html; 2 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.
Youtube; Merci Retrieval System X Series Animation; uploaded Mar. 16, 2009 (product information); posted on May 7, 2009 by SSMDePaul, time 1:09, retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
International Search Report and Written Opinion for International App. No. PCT/US21/35965, Date of Filing: Jun. 4, 2021, Applicant: Inari Medical, Inc., dated Sep. 28, 2021, 12 pages.
International Search Report and Written Opinion for International App. No. PCT/US21/45072 Date of Filing: Aug. 6, 2021, Applicant: Inari Medical, Inc., dated Jan. 20, 2022, 10 pages.
International Search Report and Written Opinion for International App. No. PCT/US21/58793; Date of Filing: Nov. 10, 2021, Applicant: Inari Medical, Inc., dated Mar. 16, 2022, 13 pages.
International Search Report and Written Opinion for International App. No. PCT/US21/59718; Date of Filing: Nov. 17, 2021, Applicant: Inari Medical, Inc., dated Mar. 22, 2022, 13 pages.
International Search Report and Written Opinion for International App. No. PCT/US21/59735; Date of Filing: Nov. 17, 2021, Applicant: Inari Medical, Inc., dated Mar. 22, 2022, 11 pages.
International Search Report and Written Opinion for International App. No. PCT/US23/60502; Date of Filing: Jan. 11, 2023, Applicant: Inari Medical, Inc., dated May 25, 2023, 9 pages.
International Search Report and Written Opinion for International App. No. PCT/US23/61256; Date of Filing: Jan. 25, 2023, Applicant: Inari Medical, Inc., dated Jun. 7, 2023, 8 pages.
Gross et al., "Dump the pump: manual aspiration thrombectomy (MAT) with a syringe is technically effective, expeditious, and cost-efficient," J NeuroIntervent Surg, 2018, 4 pages.
International Search Report and Written Opinion for International App. No. PCT/US23/60927; Date of Filing: Jan. 19, 2023, Applicant: Inari Medical, Inc., dated Jul. 20, 2023, 12 pages.
Extended European Search Report issued for EP Application No. 20877370.5, dated Oct. 17, 2023, 11 pages.
International Search Report and Written Opinion for International App. No. PCT/US23/65128; Date of Filing: Mar. 30, 2023, Applicant: Inari Medical, Inc., dated Nov. 14, 2023, 14 pages.

* cited by examiner

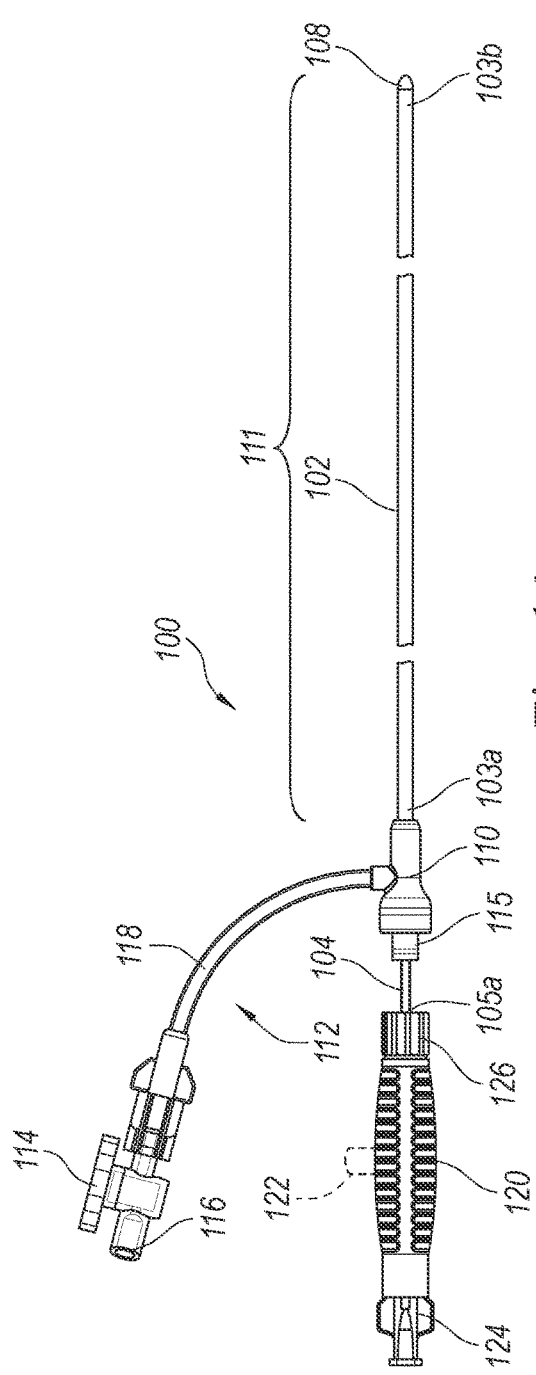
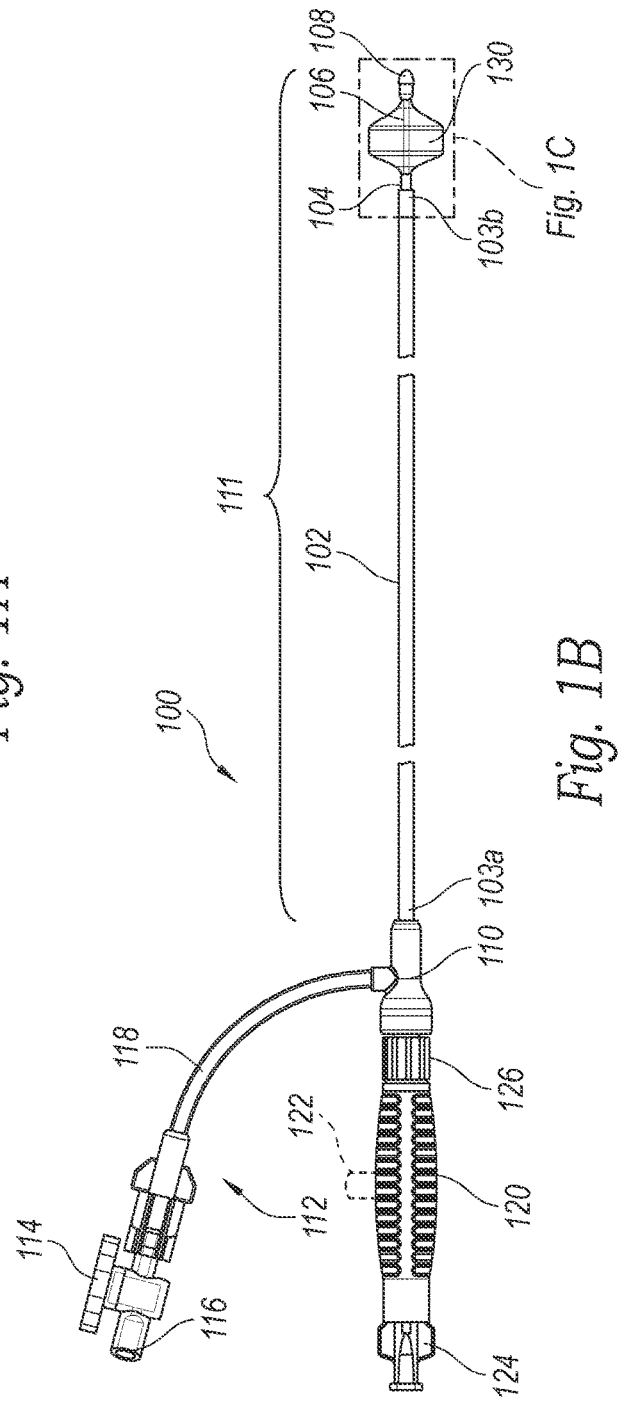

SYSTEMS, DEVICES, AND METHODS FOR TREATING VASCULAR OCCLUSIONS

CROSS-REFERENCE TO RELATED APPLICATION

This application is a continuation of U.S. patent application Ser. No. 17/072,909, filed Oct. 16, 2020, titled "SYSTEMS, DEVICES, AND METHODS FOR TREATING VASCULAR OCCLUSIONS," which claims the benefit of U.S. Provisional Patent Application No. 62/916,044, filed Oct. 16, 2019, and titled "SYSTEMS, DEVICES, AND METHODS FOR TREATING VASCULAR OCCLUSIONS," each of which is incorporated herein by reference in its entirety.

TECHNICAL FIELD

The present technology relates generally to systems, devices, and methods for the intravascular treatment of colt material (e.g., emboli and/or thrombi) within a blood vessel of a human patient. In particular, some embodiments of the present technology relate to expandable devices for engaging and removing clot material.

BACKGROUND

Thromboembolic events are characterized by an occlusion of a blood vessel. Thromboembolic disorders, such as stroke, pulmonary embolism, heart attack, peripheral thrombosis, atherosclerosis, and the like, affect many people. These disorders are a major cause of morbidity and mortality.

When an artery is occluded by a clot, tissue ischemia develops. The ischemia will progress to tissue infarction if the occlusion persists. However, infarction does not develop or is greatly limited if the flow of blood is reestablished rapidly. Failure to reestablish blood flow can accordingly lead to the loss of limb, angina pectoris, myocardial infarction, stroke, or even death.

In the venous circulation, occlusive material can also cause serious harm. Blood clots can develop in the large veins of the legs and pelvis, a common condition known as deep venous thrombosis (DVT). DVT commonly occurs where there is a propensity for stagnated blood (e.g., long distance air travel, immobility, etc.) and clotting (e.g., cancer, recent surgery, such as orthopedic surgery, etc.). DVT can obstruct drainage of venous blood from the legs leading to swelling, ulcers, pain and infection. DVT can also create a reservoir in which blood clots can collect and then travel to other parts of the body including the heart, lungs, brain (stroke), abdominal organs, and/or extremities.

In the pulmonary circulation, the undesirable material can cause harm by obstructing pulmonary arteries—a condition known as pulmonary embolism. If the obstruction is upstream, in the main or large branch pulmonary arteries, it can severely compromise total blood flow within the lungs, and therefore the entire body. This can result in low blood pressure and shock. If the obstruction is downstream, in large to medium pulmonary artery branches, it can prevent a significant portion of the lung from participating in the exchange of gases to the blood resulting in low blood oxygen and buildup of blood carbon dioxide.

There are many existing techniques to reestablish blood flow through an occluded vessel. Embolectomies, for example, are a surgical technique involving incising a blood vessel and placing a balloon-tipped device (such as the Fogarty catheter) at the location of the occlusion. The balloon is then inflated at a point beyond the clot and used to withdraw the obstructing material back to the point of incision. The obstructing material is then removed by the surgeon. Although such surgical techniques have been useful, exposing a patient to surgery may be traumatic and best avoided when possible. Additionally, the use of a Fogarty catheter may be problematic due to the possible risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced to a blood vessel (e.g., typically through an introducing catheter). The balloon-tipped catheter is then advanced to the point of the occlusion and inflated to dilate the stenosis. Balloon angioplasty is appropriate for treating vessel stenosis, but it is generally not effective for treating acute thromboembolisms as none of the occlusive material is removed and restenosis regularly occurs after dilation. Another percutaneous technique involves placing a catheter near the clot and infusing streptokinase, urokinase, or other thrombolytic agents to dissolve the clot. Unfortunately, thrombolysis typically takes hours to days to be successful. Additionally, thrombolytic agents can cause hemorrhage, and in many patients the thrombolytic agents cannot be used at all.

Various devices exist for performing a thrombectomy or removing other foreign material. However, such devices have been found to have structures which are either highly complex, cause trauma to the treatment vessel, or lack the ability to be appropriately fixed against the vessel. Furthermore, many of the devices have highly complex structures that lead to manufacturing and quality control difficulties as well as delivery issues when passing through tortuous or small diameter catheters. Less complex devices may allow the user to pull through the clot, particularly with inexperienced users, and such devices may not completely capture and/or collect all of the clot material.

Thus, there exists a need for improved systems and methods for embolic extraction.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIGS. 1A and 1B are side views of a clot treatment system in a pre-deployed configuration and a deployed configuration, respectively, configured in accordance with embodiments of the present technology.

DETAILED DESCRIPTION

Figure 1C:
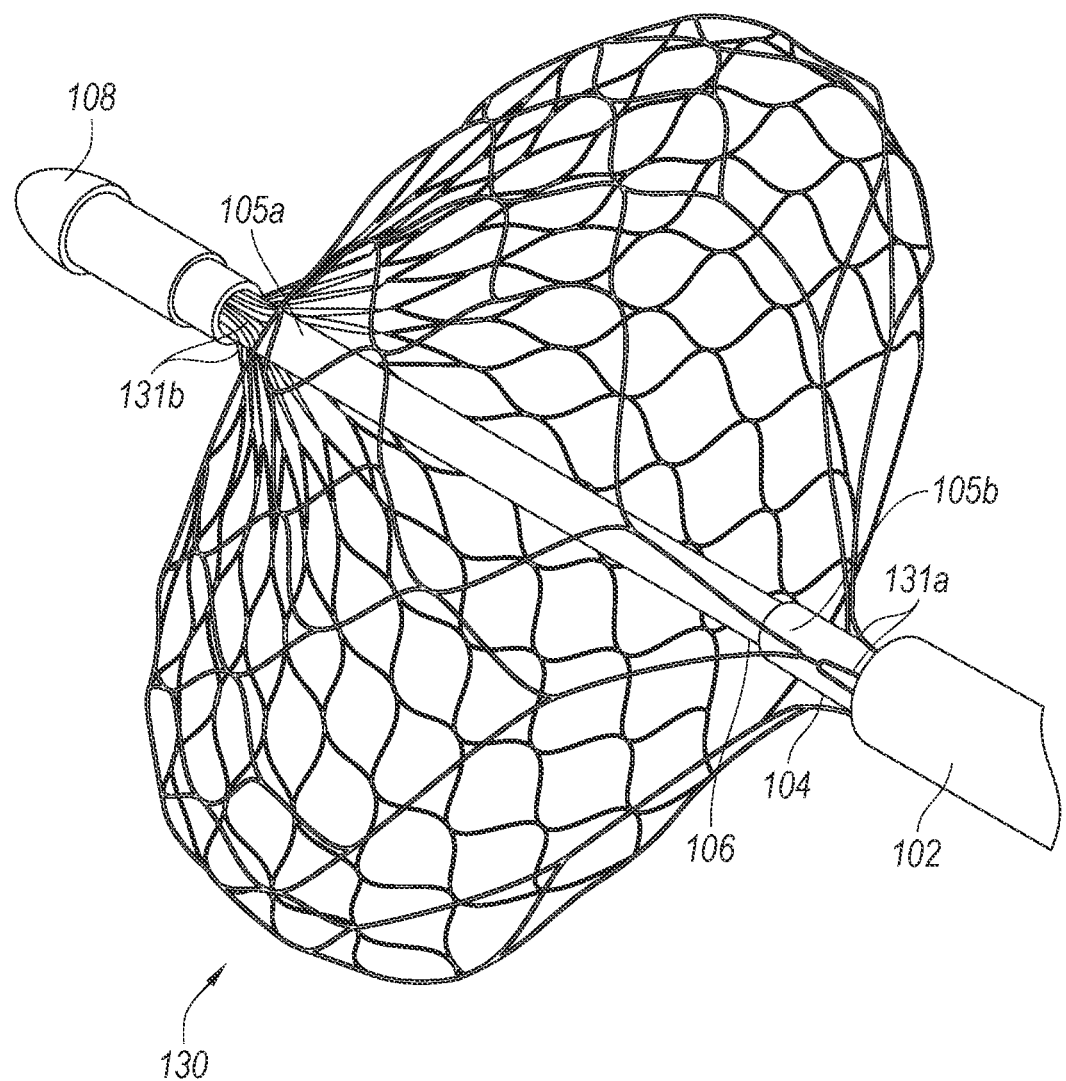
FIG. 1C is an enlarged perspective view of a distal portion of the clot treatment system shown in FIG. 1B configured in accordance with an embodiment of the present technology.

The present technology is generally directed to systems, devices, and methods for removing clot material from a blood vessel of a human patient. In some embodiments, a clot removal system can include a delivery catheter and a clot treatment device. The clot treatment device can include a plurality of interconnected struts forming a unitary structure that is movable between a compressed configuration and an expanded configuration. In the expanded configuration, the unitary structure can include (i) a proximal connection region, (ii) a proximal conical region extending from the proximal connection region, (iii) a cylindrical region extending from the proximal conical region, (iv) a distal conical region extending from the cylindrical region, and (v) a distal connection region extending from the distal conical region. In some embodiments, a first portion of the struts form first cells in the proximal conical region, and a second portion of the struts form second cells in the distal conical region that are smaller than the first cells.

In some embodiments, the system further includes a handle configured to be gripped by an operator, and a first shaft coupled between the handle and the proximal connection region of the clot treatment device. The clot treatment device can be maintained in the compressed configuration within a lumen of the delivery catheter and near a distal terminus of the delivery catheter. To move the clot treatment device to the expanded configuration, the operator can move the handle to advance the first shaft to thereby advance the clot treatment device past the distal terminus and out of the lumen of the delivery catheter. When the clot treatment device is no longer constrained by the delivery catheter, the clot treatment device can expand (e.g., self-expand) to the expanded configuration. In some embodiments, the system further includes a second shaft extending at least partially through the first shaft and coupled to the distal connection region of the clot treatment device. Relative movement between the first and second shafts can allow the clot treatment device to lengthen/shorten and to correspondingly radially expand/compress.

During a procedure to remove clot material from a blood vessel of a human patient, the clot treatment device can be expanded distal of the clot material within the blood vessel, and then retracted proximally into the clot material to capture/disrupt the clot material. In one aspect of the present technology, the larger first cells of the clot treatment device are configured to receive the clot material therethrough as the clot treatment device is pulled against the clot material, and the smaller second cells of the clot treatment device are configured to retain the clot material within the clot treatment device. In another aspect of the present technology, the clot treatment device has sufficient radial stiffness (e.g., at the cylindrical region) to inhibit the clot treatment device from slipping (e.g., not engaging) the clot material when the clot treatment device is pulled against the clot material. Accordingly, the clot treatment device can be used to capture/disrupt adhered, organized, and/or chronic clots that would otherwise be difficult to remove.

Although many of the embodiments are described below with respect to systems, devices, and methods for treating a pulmonary embolism, other applications and other embodiments in addition to those described herein are within the scope of the technology (e.g., intravascular procedures other than the treatment of emboli, intravascular procedures for treating cerebral embolism, intravascular procedures for treating deep vein thrombosis (DVT), etc.). Additionally, several other embodiments of the technology can have different configurations, states, components, or procedures than those described herein. Moreover, it will be appreciated that specific elements, substructures, advantages, uses, and/or other features of the embodiments described with reference to FIGS. 1-4F can be suitably interchanged, substituted or otherwise configured with one another in accordance with additional embodiments of the present technology. Furthermore, suitable elements of the embodiments described with reference to FIGS. 1-4F can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1-4F.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," etc. are not meant to limit the referenced component to use in a specific orientation. It will be appreciated that such designations refer to the orientation of the referenced component as illustrated in the Figures; the systems and devices of the present technology can be used in any orientation suitable to the user.

FIGS. 1A and 1B are side views of a clot treatment or clot removal system 100 ("system 100") configured in accordance with embodiments of the present technology. The system 100 is in a constrained/pre-deployment configuration in FIG. 1A, and the system 100 is in an expanded/deployed configuration in FIG. 1B. Referring to FIGS. 1A and 1B together, in the illustrated embodiment the system 100 includes a delivery catheter 102 (e.g., a tube, a shaft, etc.; which can also be referred to herein as an outer shaft) defining a lumen and having a proximal end portion 103a and a distal end portion 103b. The proximal end portion 103a of the delivery catheter 102 is coupled to a hub 110, such as a sealable hub, valve, etc. The lumen of the delivery catheter 102 can be fluidly coupled to a port assembly 112 via the hub 110.

In the illustrated embodiment, the port assembly 112 includes a fluid control device 114 fluidly coupled between (i) a port connector 116 (e.g., a Luer connector/fitting) and (ii) a tubing section 118 coupled to the hub 110 (e.g., to a branch or side port of the hub 110). The fluid control device 114 is actuatable to fluidly connect the lumen of the delivery catheter 102 to the port connector 116. In the illustrated embodiment, the fluid control device 114 is a stopcock while, in other embodiments, the fluid control device 114 can be a clamp, valve, and/or other suitable fluid control device. During a clot removal procedure using the system 100, various components (e.g., syringes, vacuum sources, etc.) can be coupled to the port connector 116 to remove fluid from and/or inject fluid into the lumen of the delivery catheter 102. For example, in some embodiments a syringe or other pressure source can be coupled to the port connector 116 and used to draw a vacuum while the fluid control device 114 is closed, and the fluid control device 114 can then be opened to instantaneously or nearly instantaneously apply the vacuum to the lumen of the delivery catheter 102 (e.g., to generate suction at the distal portion 103b for removing clot material). In other embodiments, a constant vacuum source (e.g., a pump) can be coupled to the port assembly 112 to provide constant aspiration of the lumen of the delivery catheter 102. In some embodiments, flushing fluid (e.g., saline) can be injected through the port assembly 112 to flush the lumen of the delivery catheter 102.

In the illustrated embodiment, the system 100 further includes an intermediate shaft 104 (e.g., a catheter, tube, etc.) extending at least partially through the lumen of the delivery catheter 102 and defining a lumen, and an inner shaft 106 (e.g., a catheter, tube, etc.) extending at least partially through the lumen of the intermediate shaft 104. Accordingly, in some embodiments the delivery catheter 102, the intermediate shaft 104, and the inner shaft 106 are coaxially aligned/arranged. The system 100 further includes a clot treatment device 130 coupled to the intermediate shaft 104 and the inner shaft 106. The delivery catheter 102, the intermediate shaft 104, the inner shaft 106, and the clot treatment device 130 can collectively be referred to as a treatment portion 111 (e.g., an insertion portion) of the system 100. As described in greater detail below with reference to FIGS. 3-4F, the treatment portion 111 is configured to be inserted through a guide catheter to position the clot treatment device 130 at a treatment site during a clot removal procedure.

As described in greater detail below with reference to FIGS. 2A-2C, the clot treatment device 130 can be a self-expanding unitary structure comprising a plurality of interconnected struts. In the pre-deployment configuration shown in FIG. 1A, the clot treatment device 130 is constrained within the delivery catheter 102 and thus obscured. In the deployed configuration shown in FIG. 1B, the clot treatment device 130 extends past the distal end portion 103b of the delivery catheter 102 (e.g., a distal terminus of the delivery catheter 102) and is radially expanded.

FIG. 1C is an enlarged perspective view of a distal portion of the system 100 shown in FIG. 1B configured in accordance with an embodiment of the present technology. In the illustrated embodiment, the intermediate shaft 104 includes a distal end portion 105b coupled to a proximal portion 131a of the clot treatment device 130. In some embodiments, the proximal portion 131a of the clot treatment device 130 includes a plurality of struts that are gathered together and secured to the distal end portion 105b of the intermediate shaft 104. For example, the struts at the proximal portion 131a of the clot treatment device 130 can be secured to the outer surface of the intermediate shaft 104 via adhesives, fasteners, a hub or other device, etc. The inner shaft 106 includes a distal end portion 107 coupled to a distal portion 131b of the clot treatment device 130. In some embodiments, the distal portion 131b of the clot treatment device 130 includes a plurality of struts that are gathered together and secured to the distal end portion 107 of the inner shaft 106 via a friction fit, pressure fit, etc., between the inner shaft 106 and a distal tip 108 (e.g., an atraumatic tip). In other embodiments, the struts at the distal portion 131b of the clot treatment device 130 can be secured to the outer surface of the inner shaft 106 via adhesives, fasteners, a hub or other device, etc.

Referring again to FIGS. 1A and 1B together, the intermediate shaft 104 includes a proximal end portion 105a coupled to the handle 120 (e.g., to a distal portion of the handle 120) to operably couple the handle 120 to the clot treatment device 130. Accordingly, the intermediate shaft 104 extends between and operably couples the handle 120 and the clot treatment device 130. In some embodiments, a proximal end portion of the inner shaft 106 (obscured in FIGS. 1A and 1B) is not coupled to any portion of the system 100 and floats within the lumen of the intermediate shaft 104. In one aspect of the present technology, this arrangement allows the inner shaft 106 to move relative to the intermediate shaft 104 in response to external forces on the clot treatment device 130, thereby allowing the clot treatment device 130 to elongate/shorten longitudinally and to correspondingly radially compress/expand. In other embodiments, the proximal end portion of the inner shaft 106 can be coupled to an actuation mechanism 122 (shown in dashed lines in FIGS. 1A and 1B) of the handle 120. The actuation mechanism 122 can be configured to drive the inner shaft 106 proximally and/or distally to shorten and/or elongate, respectively, the clot treatment device 130. More specifically, in some embodiments distal movement of the actuation mechanism 122 relative to the handle 120 can move the inner shaft 106 distally relative to the intermediate shaft 104 to lengthen and radially compress the clot treatment device 130, while proximal movement of the actuation mechanism 122 relative to the handle 120 can move the inner shaft 106 proximally relative to the intermediate shaft 104 to shorten and radially expand the clot treatment device 130.

In the illustrated embodiment, the handle 120 further includes a proximal hub 124, such as a Luer hub, configured to receive a guidewire (not shown) therethrough. The handle 120, the inner shaft 106, and the tip 108 can together define a lumen for receiving the guidewire therethrough. In some embodiments, the guidewire can have a diameter of about 0.035 inch, about 0.018 inch, less than about 0.1 inch, less than about 0.05 inch, etc. In some embodiments, the handle 120 further includes a lock feature 126 such as, for example, a spinlock or a push-in-and-turn lock. The lock feature 126 is configured to selectively engage (e.g., lockingly engage) with a mating feature 115 of the hub 110. Locking the handle 120 to the hub 110 via the lock feature 126 and the mating feature 115 secures the position of the intermediate shaft 104 relative to the delivery catheter 102. In the illustrated embodiment, the intermediate shaft 104 is longer than the delivery catheter 102 such that a portion of the intermediate shaft 104 and the clot treatment device 130 extend distally from the distal end portion 103b of the delivery catheter 102 when the handle 120 is lockingly engaged with the hub 110.

To deploy the clot treatment device 130 from the pre-deployment configuration (FIG. 1A) to the deployed configuration (FIG. 1B), an operator can move the handle 120 distally toward the hub 110 and/or can move the hub 110 toward the handle 120. This movement advances the intermediate shaft 104 distally through the delivery catheter 102 and pushes the clot treatment device 130 distally out of the delivery catheter 102. The clot treatment device 130 can self-expand as it is released from the lumen of the delivery catheter 102. When the handle 120 abuts the hub 110, the operator can actuate the lock feature 126 to secure the position of the intermediate shaft 104 relative to the delivery catheter 102 to, for example, maintain the clot treatment device 130 in the deployed configuration.

In some embodiments, proximal movement of the handle 120 and/or distal movement of the hub 110 (e.g., from the position shown in FIG. 1B to the position shown in FIG. 1A) can retract the clot treatment device 130 back into the delivery catheter 102. That is, in some embodiments the clot treatment device 130 can be resheathed within the delivery catheter 102. In such embodiments, the clot treatment device 130 can be repeatedly expanded and then retracted and compressed into the delivery catheter 102. In some embodiments, the tip 108 is configured (e.g., sized and shaped) to abut the distal end portion 103b of the delivery catheter 102 in the pre-deployment configuration (FIG. 1A). This can inhibit or even prevent the clot treatment device 130 from being pulled fully through the delivery catheter 102 and, in some embodiments, can substantially seal the lumen of the delivery catheter 102. In other embodiments, the tip 108 is sized and shaped to allow the tip 108—and thus the entire clot treatment device 130—to be retracted through the delivery catheter 102.

Figure 2A:
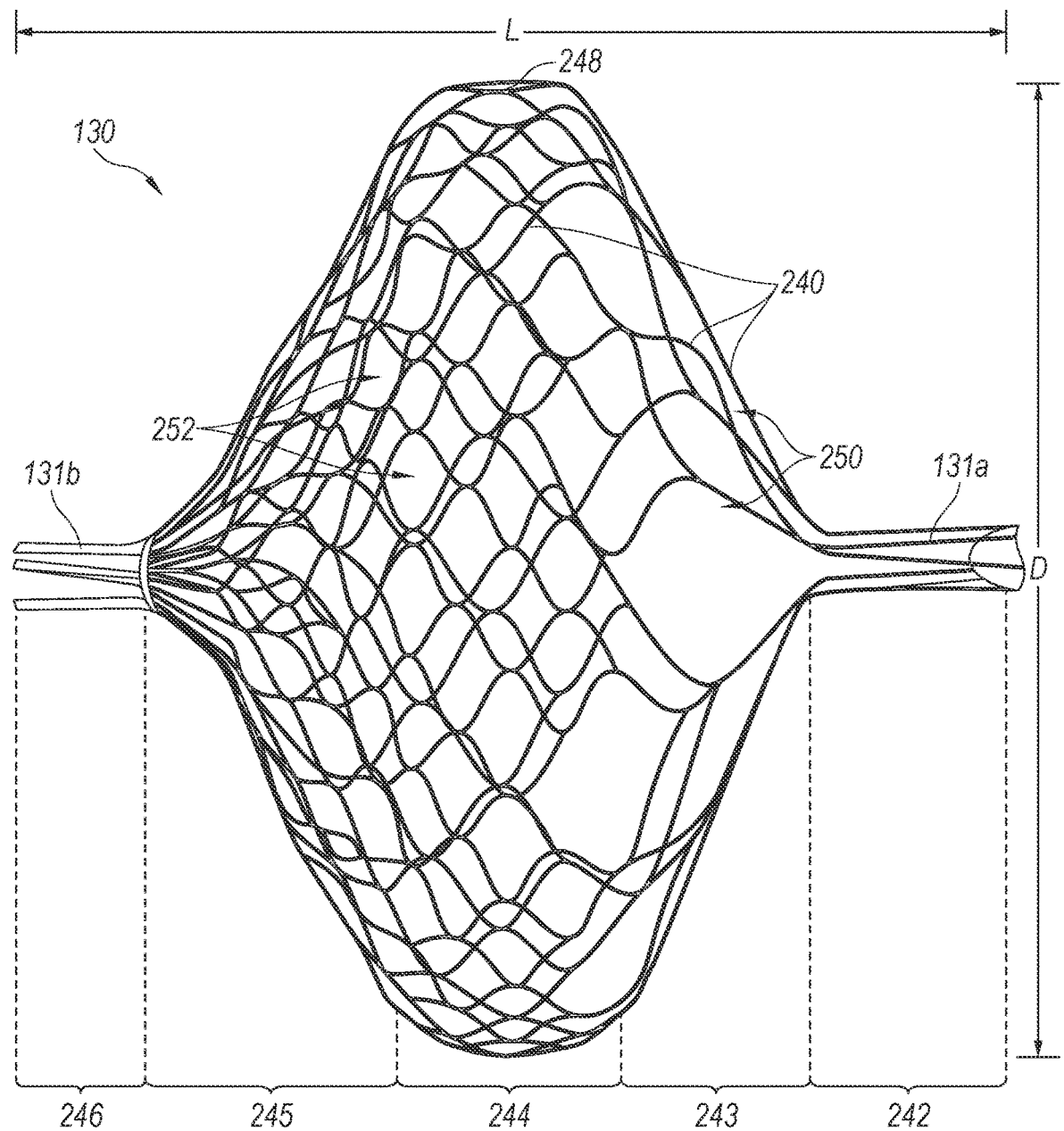
FIGS. 2A-2C are a side view, a proximally-facing perspective view, and a distally-facing perspective view, respectively, of a clot treatment device of the clot treatment system of FIGS. 1A-1C configured in accordance with embodiments of the present technology.
Figure 2B:
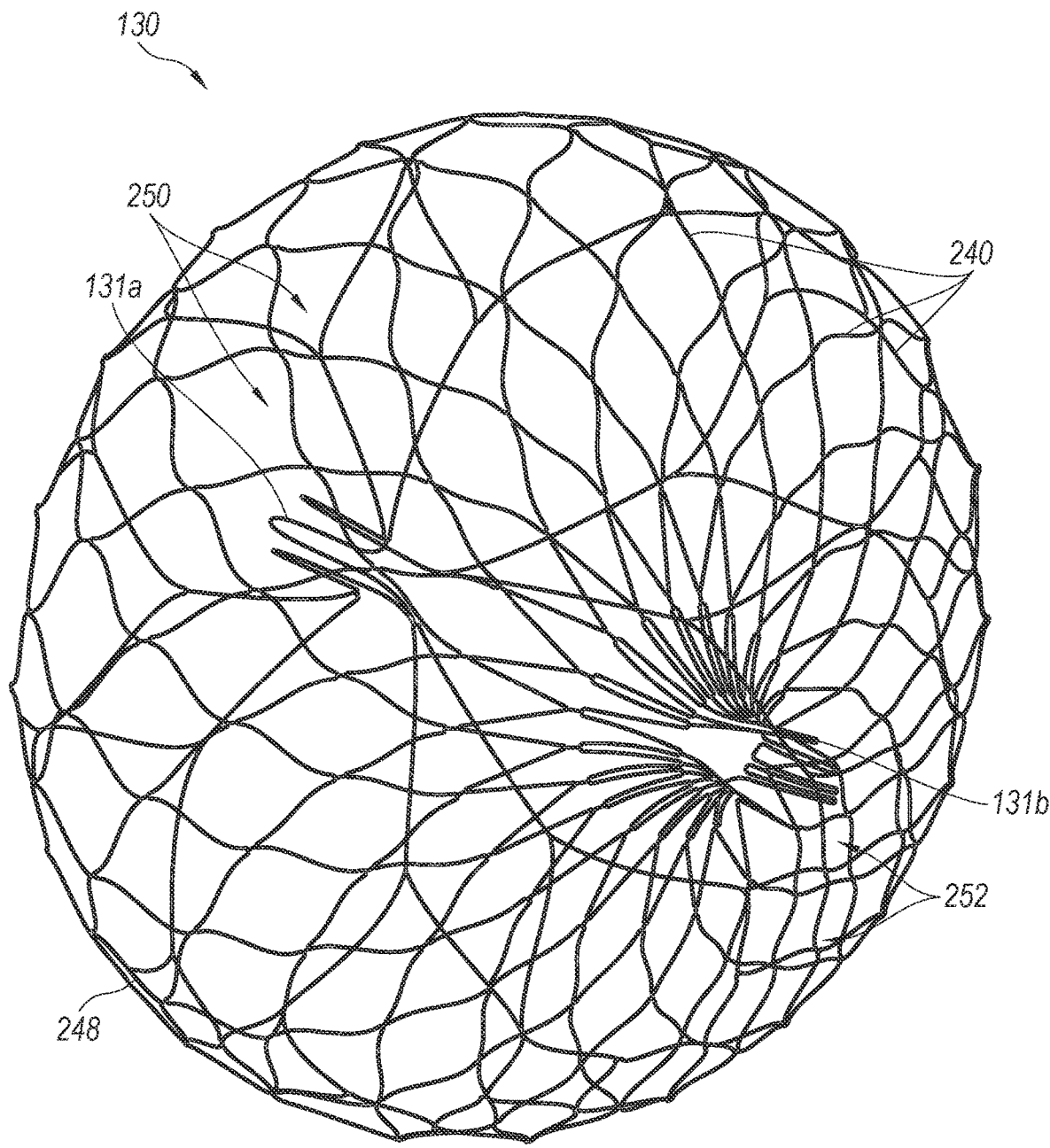
Figure 2C:
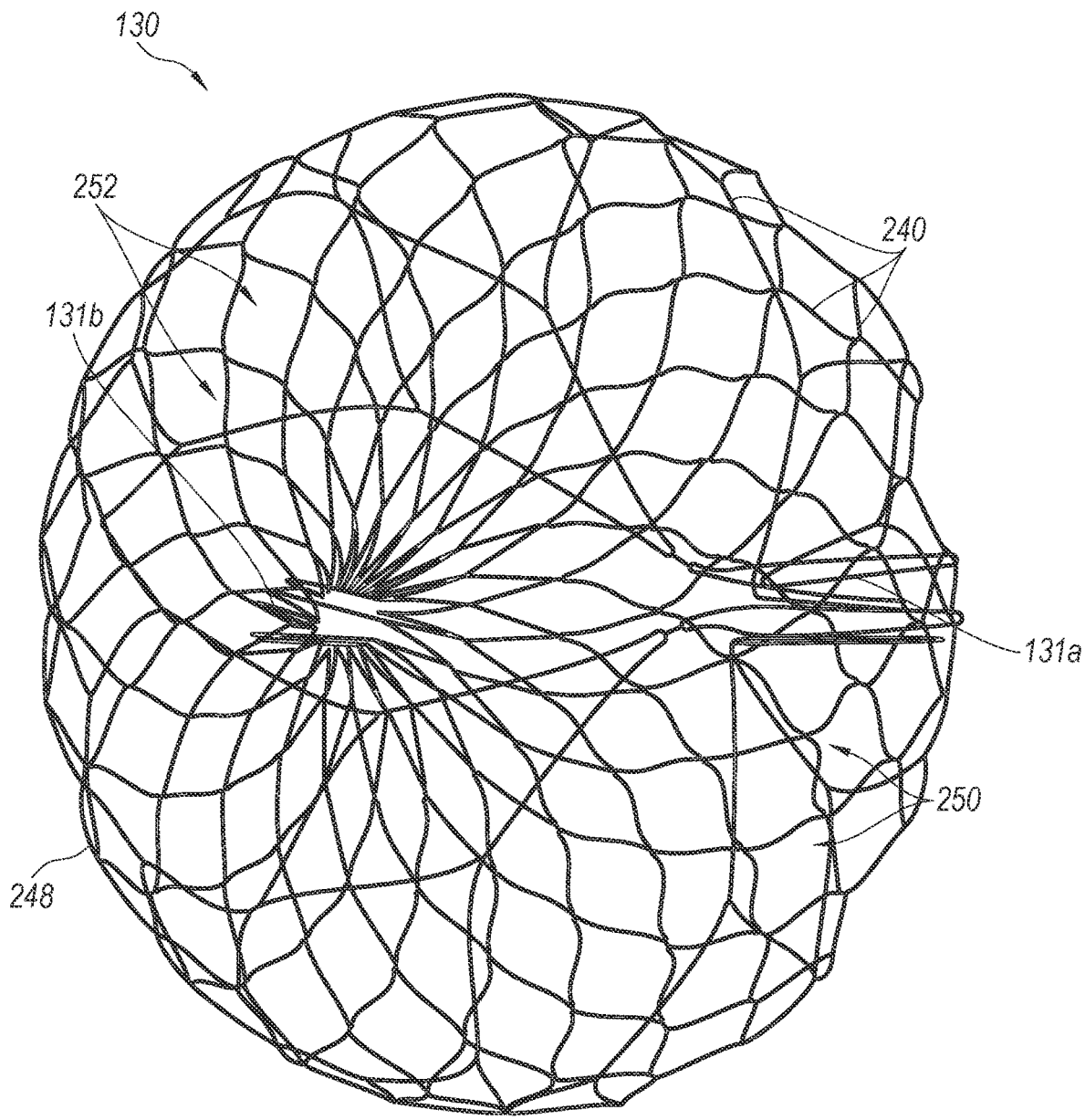

FIGS. 2A-2C are a side view, a proximally-facing perspective view, and a distally-facing perspective view, respectively, of the clot treatment device 130 in the expanded configuration in accordance with embodiments of the present technology. Referring to FIGS. 2A-2C together, the clot treatment device 130 comprises a plurality of struts 240 that together define a plurality of first cells 250 (e.g., interstices, pores, openings, etc.) and a plurality of second cells 252. The struts 240 can have a variety of shapes and sizes and, in some embodiments, the struts 240 can have a thickness and/or diameter between about 0.0125-0.150 inch, between about 0.075-0.125 inch, between about 0.090-0.150 inch, and/or other dimensions. In general, the struts 240 together form a unitary structure that is configured to engage, capture, disrupt, and/or separate a portion of a thrombus (e.g., a vascular thrombus) from a blood vessel containing the thrombus.

In the illustrated embodiment, (i) the first cells 250 generally face proximally while the second cells 252 generally face distally, and (ii) the first cells 250 are larger than the second cells 252. As best seen in FIG. 2A, the clot treatment device 130 includes (i) a first region 242 including the proximal portion 131a, (ii) a second region 243 distal of the first region 242, (iii) a third (e.g., central) region 244 distal of the second region 243, (iv) a fourth region 245 distal of the third region 244, and (v) a fifth region 246 distal of the fourth region 245 and including the distal portion 131b. In the illustrated embodiment, the struts 240 are gathered together (e.g. positioned proximate one another) at the first and fifth regions 242, 246 to facilitate their connection to the intermediate and inner shafts 104, 106, respectively, as shown in FIG. 1C. The second region 243 can have a generally conical shape that tapers (e.g., radially narrows) in the proximal direction. Similarly, the fourth region 245 can have a generally conical shape that tapers in the distal direction. The third region 244 can have a generally tubular/cylindrical shape including, for example a generally flat outer strut surface/boundary 248. Moreover, in the illustrated embodiment the first and second regions 242, 243 have fewer of the struts 240 than the fourth and fifth regions 245, 246 to thereby define the larger first cells 250. Conversely, the fourth and fifth regions 245, 246 have more of the struts 240 than the first and second regions 242, 243 to thereby define the smaller second cells 252. The third region 244 can be a transition region in which the number of the struts 240 increases in the proximal direction (e.g., toward the fourth region 245) such that some of the first cells 250 abut some of the second cells 252 in the third region 244. In other embodiments, the first cells 250 can be formed only in the second region 243, can occupy the entire third region 244, can extend into the fourth region 245, etc.

In some embodiments, the clot treatment device 130 is made from a shape memory material such as a shape memory alloy and/or a shape memory polymer. For example, the clot treatment device 130 can comprise nitinol and/or a nitinol alloy. Similarly, the clot treatment device 130 can be made using a variety of techniques including welding, laser welding, cutting, laser cutting, expanding, etc. For example, in some embodiments the clot treatment device 130 can first be laser cut from a piece of nitinol (e.g., a nitinol tube), and then further shaped using a heat setting process such that the clot treatment device 130 has the illustrated shape in the expanded configuration. For example, as is known in the art of heat setting nitinol structures, a fixture, mandrel, or mold may be used to hold the clot treatment device 130 in its desired configuration, and then the clot treatment device 130 can be subjected to an appropriate heat treatment such that the struts 240 of the clot treatment device 130 assume or are otherwise shape-set to the outer contour of the mandrel or mold. The heat setting process may be performed in an oven or fluidized bed, as is well-known. Therefore, the heat setting process can impart a desired shape, geometry, bend, curve, serration, scallop, void, hole, etc., in the super-elastic and/or shape memory material or materials used to form the clot treatment device 130. Accordingly, the clot treatment device 130 may be radially constrained without plastic deformation and will self-expand on release of the radial constraint.

In general, the size of the clot treatment device 130 can be selected based on the size (e.g., diameter) of the blood vessel from which thrombus is to be extracted. In some embodiments, in a fully-expanded configuration unconstrained within a vessel, the clot treatment device 130 can have a length L (FIG. 2A) of between about 0.025-1.50 inches, between about 0.70-1.15 inches, etc. In some embodiments, in the fully-expanded position unconstrained within a vessel, the clot treatment device 130 can have a maximum diameter D (FIG. 2A; e.g., at the third region 244) of between about 0.025-1.5 inches, between about 0.71-1.34 inches, etc.

The clot treatment device 130 is configured (e.g., shaped, sized, angled, formed, etc.) to engage, disrupt, and/or capture clot material from within a blood vessel when the clot treatment device 130 is retracted through/against the clot material in the expanded configuration. For example, as described in greater detail below with reference to FIGS. 3-4F, the clot treatment device 130 can be withdrawn proximally through/against the clot material. In one aspect of the present technology, the larger first cells 250 are configured to receive the clot material therethrough as the clot treatment device 130 is pulled against the clot material, and the smaller second cells 252 (and associated struts 240) are configured to retain the clot material within the clot treatment device 130. In another aspect of the present technology, the clot treatment device 130 has sufficient radial stiffness (e.g., at the third region 244) to inhibit the clot treatment device 130 from slipping (e.g., not engaging) the clot material when the clot treatment device 130 is pulled against the clot material. Accordingly, the clot treatment device 130 can be used to capture/disrupt adhered, organized, and/or chronic clots. In some embodiments, portions of the struts 240 (e.g., at the second region 243) can be sharpened and/or can include a cutting element (e.g., a knife or knife edge) attached thereto or otherwise integrated with to further facilitate disruption/cutting of the clot material.

Figure 3:
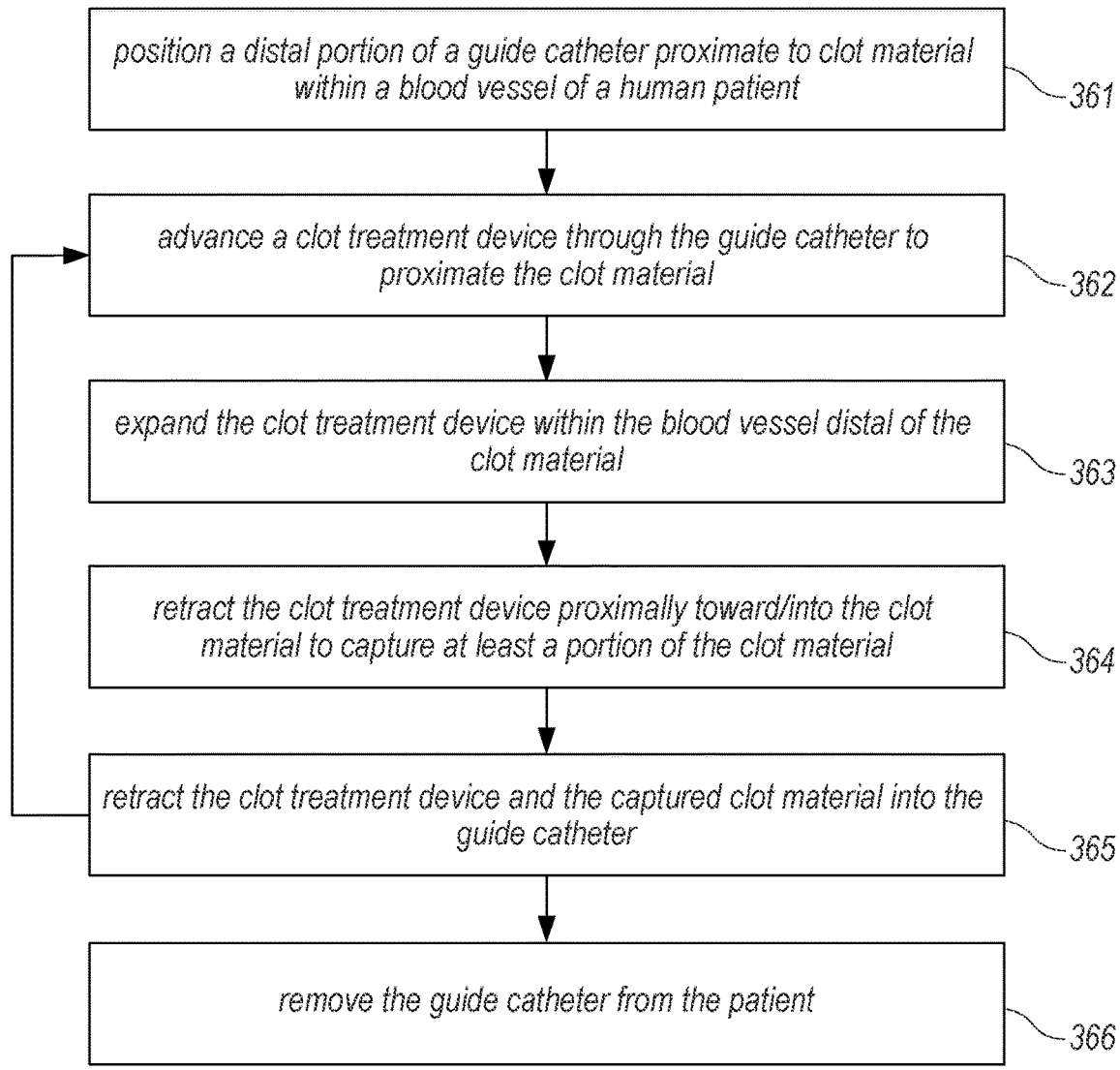
FIG. 3 is a flow diagram of a process or method for operating the clot treatment system to remove clot material from within a blood vessel of a human patient in accordance with an embodiment of the present technology.

FIG. 3 is a flow diagram of a process or method 360 for operating the system 100 to remove clot material from within a blood vessel (e.g., a pulmonary blood vessel) of a patient (e.g., a human patient) in accordance with an embodiment the present technology. FIGS. 4A-4F are schematic illustrations of a distal portion of the system 100 inserted through a guide catheter 470 during a procedure to remove clot material PE from a blood vessel BV of a patient in accordance with embodiments of the present technology. Although some features of the method 360 are described in the context of the embodiments shown in FIGS. 4A-4F for the sake of illustration, one skilled in the art will readily understand that the method 360 can be carried out using other suitable systems and/or devices described herein.

Figure 4A:
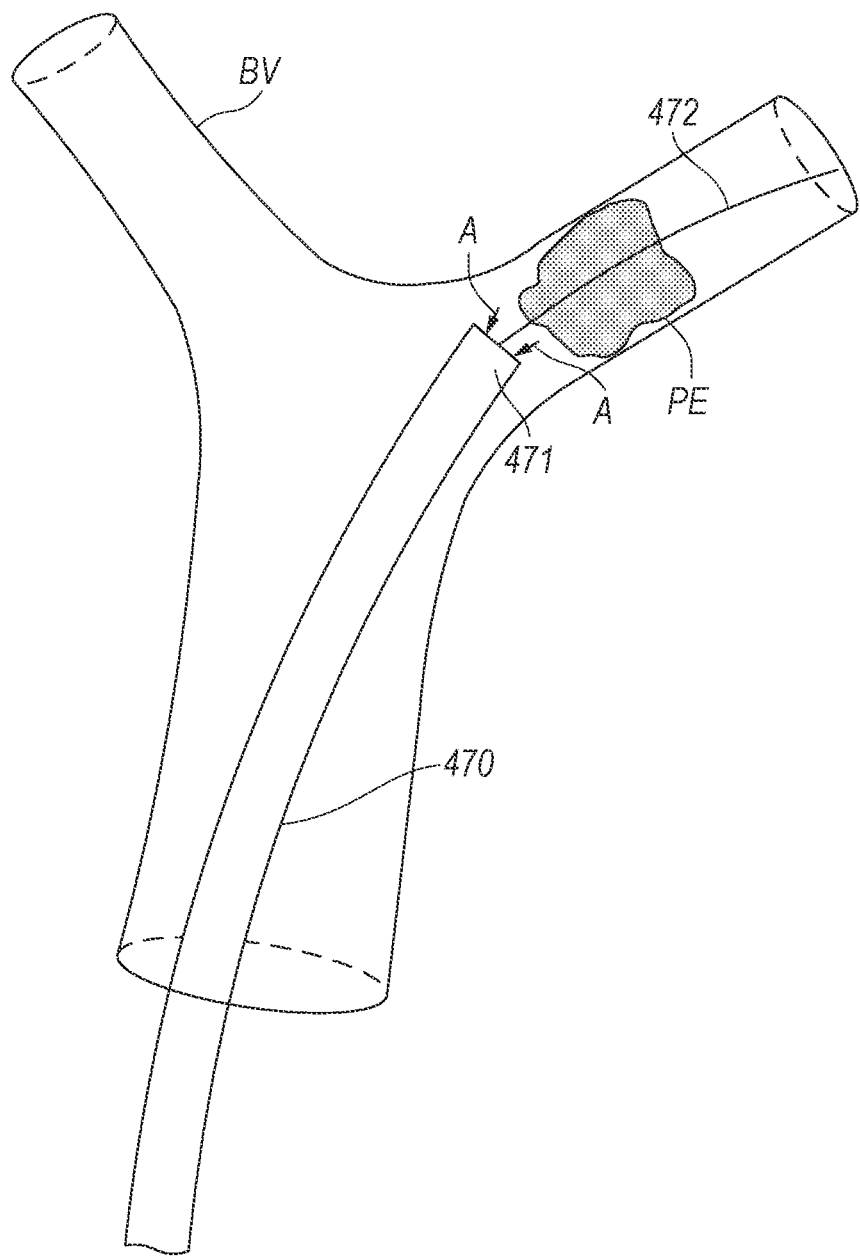
FIGS. 4A-4F are schematic illustrations of a distal portion of the clot treatment system during a procedure to remove clot material from a blood vessel of a human patient in accordance with embodiments of the present technology.

With reference to FIGS. 3 and 4A, at block 361, the method 360 can include positioning a distal portion 471 of the guide catheter 470 proximate to the clot material PE within the blood vessel BV (e.g., at a treatment site). In the illustrated embodiment, a distal terminus of the guide catheter 470 is positioned proximate to a proximal portion of the clot material PE. However, in other embodiments the distal terminus of the guide catheter 470 can be positioned at least partially within the clot material PE, or the distal terminus of the guide catheter 470 can be positioned distal of the clot material PE. Access to the blood vessel BV can be achieved through the patient's vasculature, for example, via the femoral vein. In some embodiments, such as when the blood vessel BV is a pulmonary blood vessel, an introducer (e.g., a Y-connector with a hemostasis valve; not shown) is connected to the guide catheter 470 and can be partially inserted into the femoral vein. A guidewire 472 can be guided into the femoral vein through the introducer and navigated through the right atrium, the tricuspid valve, the right ventricle, the pulmonary valve, and into the main pulmonary artery. Depending on the location of the clot material PE, the guidewire 472 can be guided to one or more of the branches of the right pulmonary artery and/or the left pulmonary artery. In some embodiments, the guidewire 472 can be extended entirely or partially through the clot material PE. In other embodiments, the guidewire 472 can be extended to a location just proximal of the clot material PE. After positioning the guidewire 472, the guide catheter 470 can be placed over the guidewire 472 and advanced to the position proximate to the clot material PE as illustrated in FIG. 4A.

In some embodiments, a pressure source can be coupled to the guide catheter 470 and used to aspirate the lumen of the guide catheter 470 to, for example, generate suction (e.g., as indicated by arrows A) to suck/draw all or a portion of the clot material PE into the guide catheter 470. For example, in some embodiments a vacuum can be precharged (e.g., in a syringe fluidly coupled to the lumen of the guide catheter 470) and the vacuum can be applied to the lumen of the guide catheter 470 to instantaneously or nearly instantaneously generate suction at the distal portion 471 of the guide catheter 470 (e.g., to generate a suction pulse at the distal portion 471 of the guide catheter 470). Specific details of such methods and associated devices are disclosed in U.S. patent application Ser. No. 16/536,185, filed Aug. 8, 2019, and titled "SYSTEM FOR TREATING EMBOLISM AND ASSOCIATED DEVICES AND METHODS," which is incorporated herein by reference in its entirety.

However, even where suction is applied to remove/dislodge the clot material PE from the blood vessel BV, the suction may not be enough to dislodge/disrupt all the clot material PE. For example, many chronic (e.g., organized) clots can strongly adhere to the walls of the blood vessel BV—making it difficult to remove them. In one aspect of the present technology, the system 100 can be inserted through the guide catheter 470 before, during, and/or after suction is applied via the guide catheter 470 to engage, disrupt, and/or capture the clot material PE—even where the clot material PE is strongly adhered within the blood vessel BV.

Figure 4B:
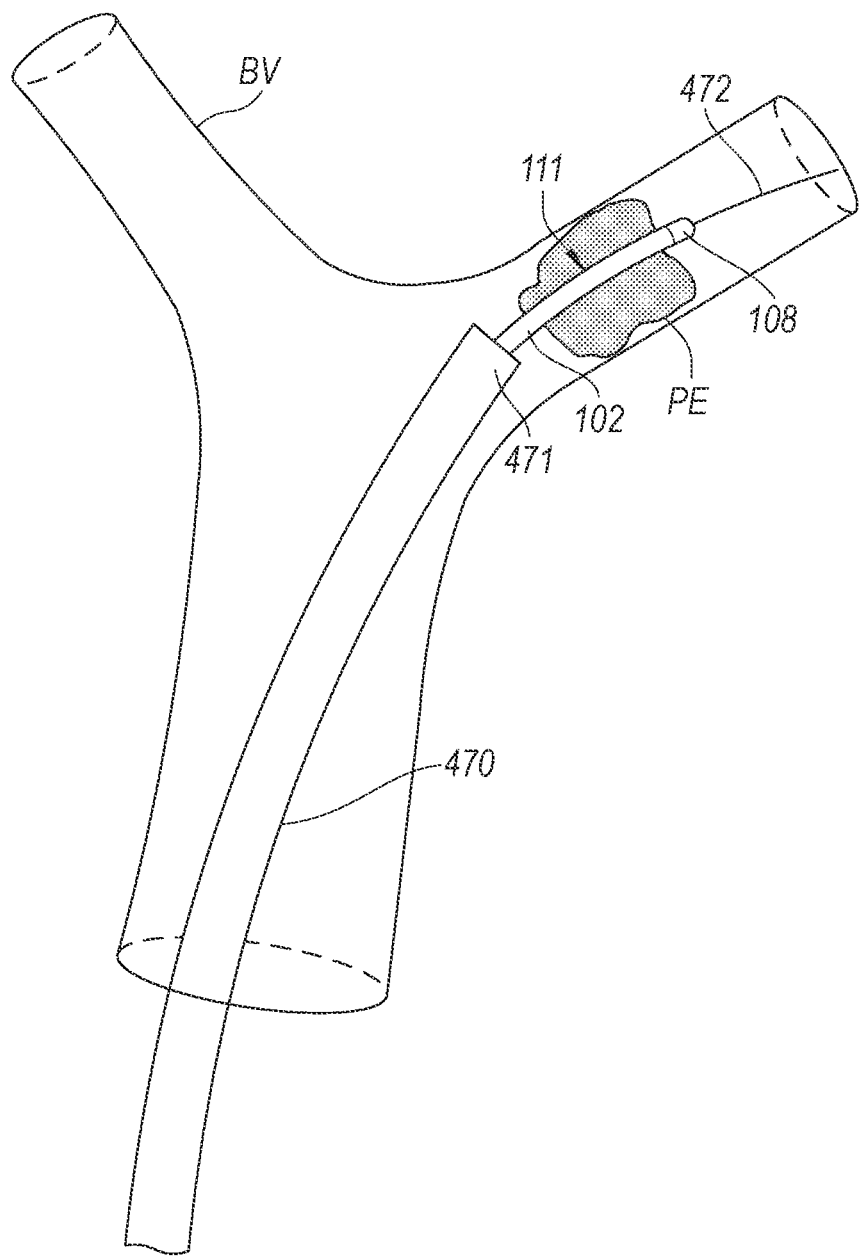

For example, with reference to FIGS. 3 and 4B, at block 362, the method 360 can include advancing the clot treatment device 130 (compressed within the delivery catheter 102 and thus obscured in FIG. 4B) through the guide catheter 470 to proximate the clot material PE. More specifically, the treatment portion 111 of the system 100 can be advanced through the guide catheter 470 in the compressed pre-deployment configuration until the tip 108 is positioned (i) distal of the distal portion 471 of the guide catheter 470 and (ii) distal of the clot material PE within the blood vessel BV. In other embodiments, the tip 108 can be positioned within the clot material PE. In some embodiments, the treatment portion 111 can be advanced over the guidewire 472 while, in other embodiments, the guidewire 472 can be omitted.

Figure 4C:
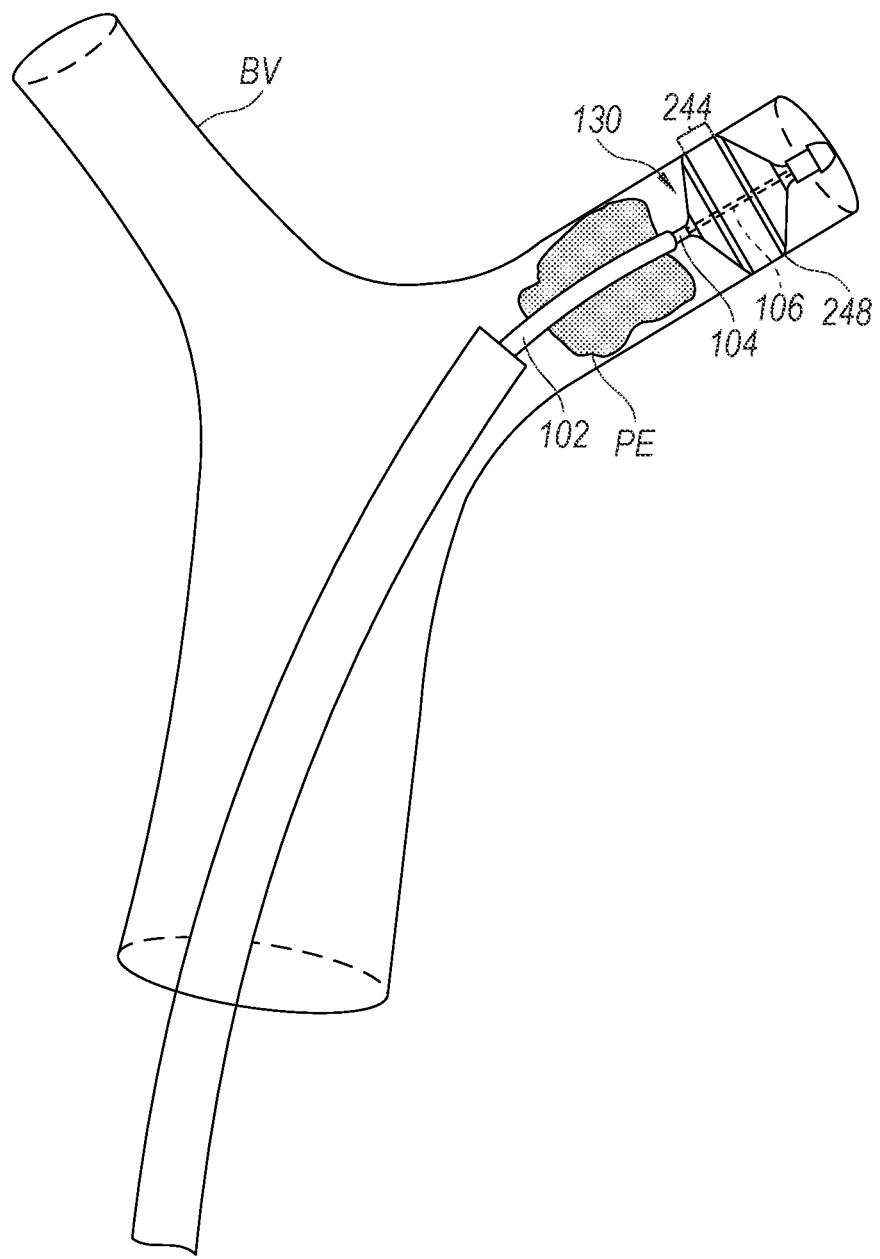

With reference to FIGS. 3 and 4C, at block 363, the method 360 can include moving the clot treatment device 130 from the compressed pre-deployment configuration to the expanded deployed configuration such that the clot treatment device 130 is expanded distal and/or partially within the clot material PE. For example, as described in detail above with reference to FIGS. 1A and 1B, an operator of the system 100 can advance the handle 120 distally toward the hub 110 and/or retract the hub 110 toward the handle 120 to move the intermediate shaft 104 relative to the delivery catheter 102 to advance the clot treatment device 130 out of the delivery catheter 102, thereby allowing the clot treatment device 130 to expand (e.g., self-expand) within the blood vessel BV. In the illustrated embodiment, the clot treatment device 130 (e.g., the outer strut surface 248 of the third region 244) contacts (e.g., engages, apposes, etc.) the wall of the blood vessel BV. In some embodiments, the clot treatment device 130 is oversized relative to the blood vessel BV such that the clot treatment device 130 exerts a radially outward force on the wall of the blood vessel BV. In other embodiments, the clot treatment device 130 can be sized such that it does not contact the walls of the blood vessel BV.

Figure 4D:
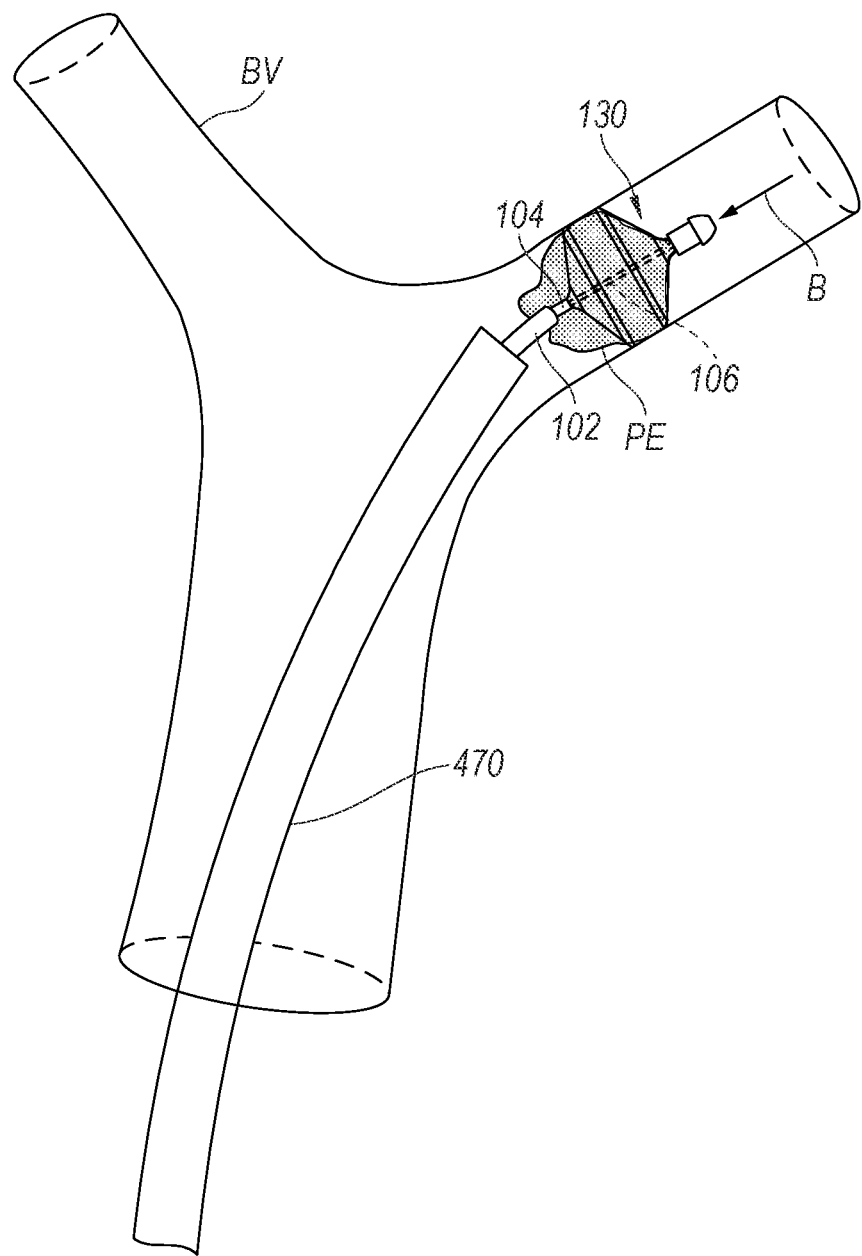

With reference to FIGS. 3 and 4D, at block 364, the method 360 can include retracting the clot treatment device 130 proximally (e.g., in the direction of arrow B) into/toward the clot material PE. More specifically, with reference to FIGS. 1A and 1B, the operator can pull the entire system 100 proximally (e.g., by gripping the hub 110) to retract the treatment portion 111 through the lumen of the guide catheter 470. As the clot treatment device 130 is retracted, the clot treatment device 130 engages the clot material PE to capture/disrupt the clot material PE. For example, the clot material PE can enter through the first cells 250 (FIGS. 2A-2C) and be retained within the clot treatment device 130 by the smaller second cells 252 (FIGS. 2A-2C). In one aspect of the present technology, the clot treatment device 130 can shear the clot material PE from the wall of the blood vessel BV even where the clot material PE is strongly adhered to the wall of the blood vessel BV.

In some embodiments, where the inner shaft 106 floats within the lumen of the intermediate shaft 104, the length L (FIG. 2A) of the clot treatment device 130 can increase as the clot treatment device 130 is pulled into/against the clot material PE and the intermediate shaft 104 moves proximally relative to the inner shaft 106. In other embodiments, where the system 100 includes the actuation mechanism 122, the operator can actuate the actuation mechanism 122 to increase the longitudinal and/or radial stiffness of the clot treatment device 130 by locking or substantially locking the relative position of the intermediate and inner shafts 104, 106.

Figure 4E:
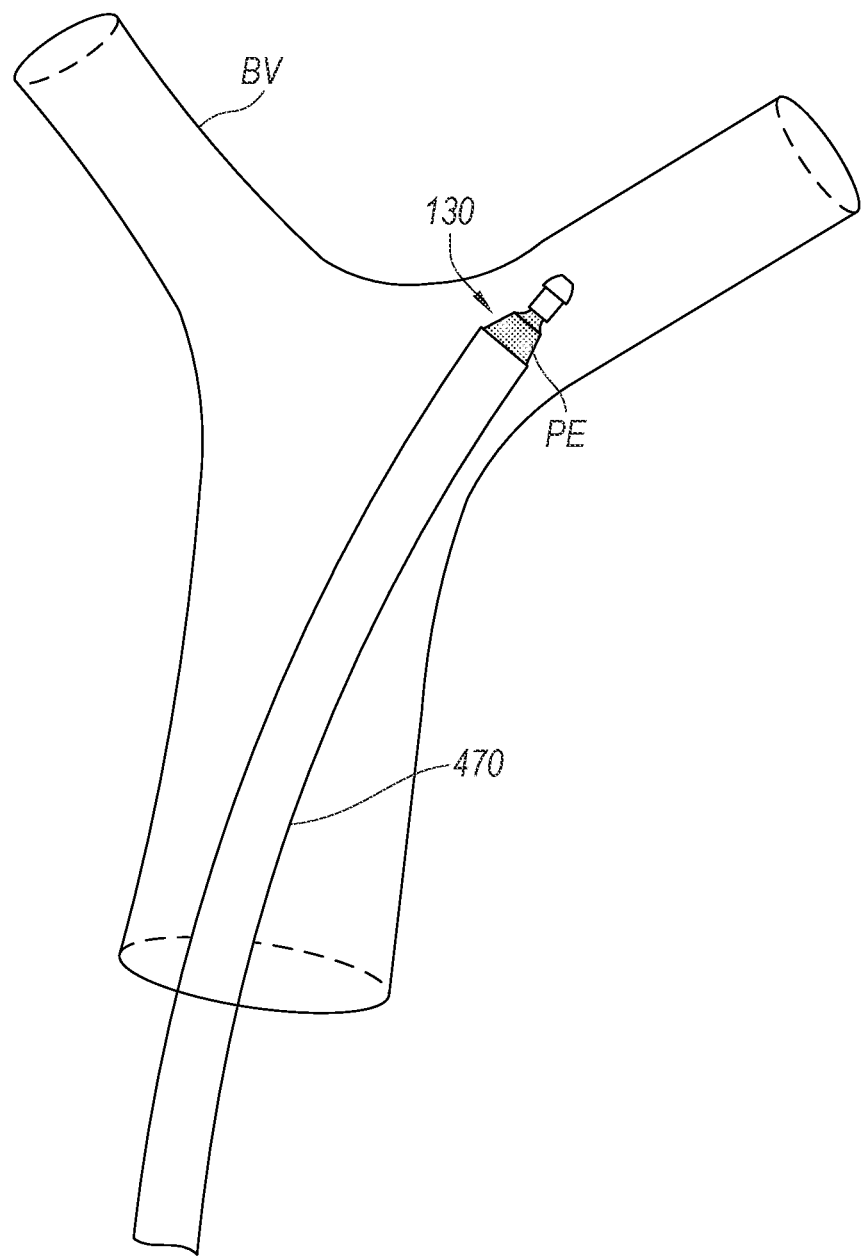
Figure 4F:
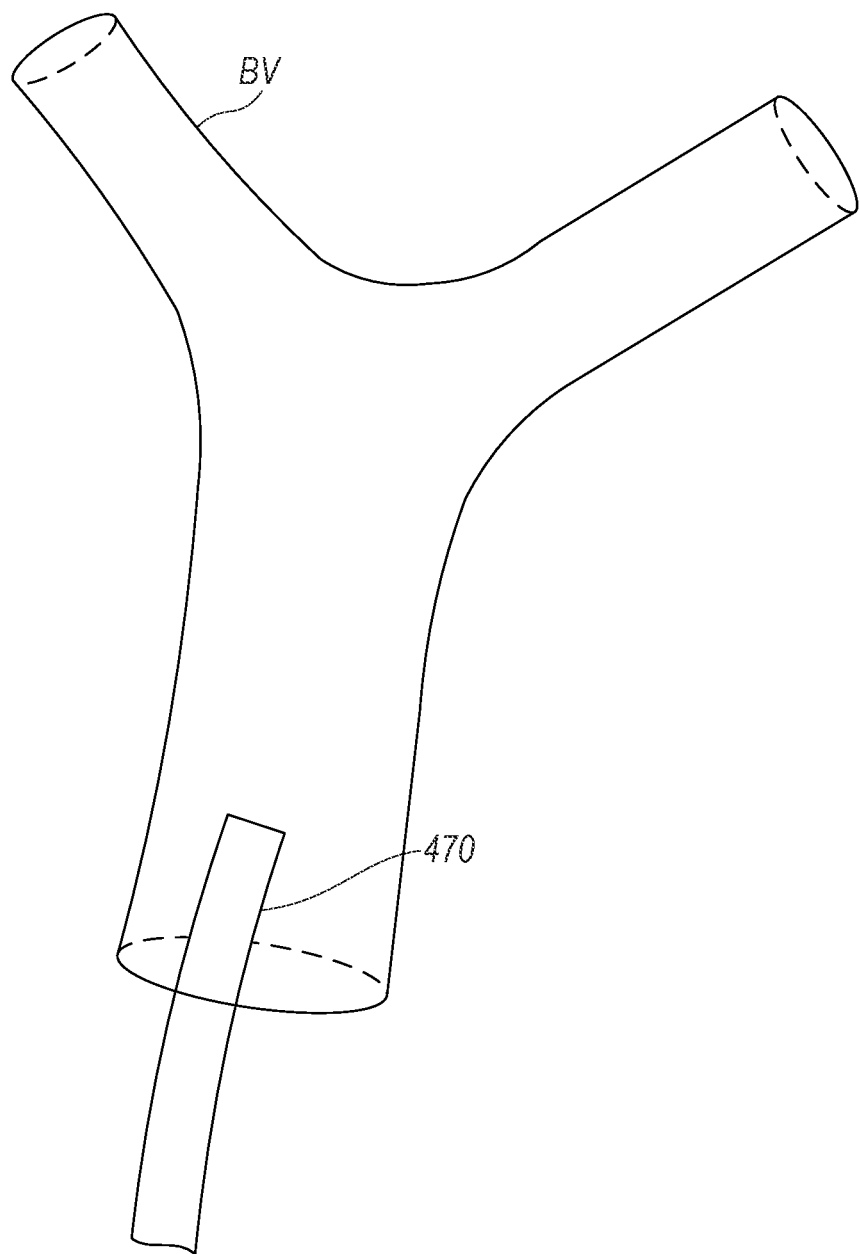

With reference to FIGS. 3 and 4E, at block 365, the method 360 can include retracting the clot treatment device 130 and the captured clot material PE into the lumen of the guide catheter 470. In some embodiments, the clot treatment device 130 can be fully removed from the guide catheter 470. In some embodiments, if any of the clot material PE remains in the blood vessel BV, the clot treatment device 130 can be cleaned and blocks 362-365 can be repeated to capture the remaining clot material PE. Alternatively, a new clot treatment device 130 can be reinserted through the guide catheter 470 to capture the remaining clot material PE. In some embodiments, the clot treatment device 130 can break apart the clot material PE without necessarily capturing the clot material PE and, after or during retraction of the clot treatment device 130, aspiration can be applied to the guide catheter 470 to suck the remaining clot material PE into the guide catheter 470. Finally, with reference to FIGS. 3 and 4F, at block 366, the method 360 can include removing the guide catheter 470 from the blood vessel BV and from the patient after a sufficient portion of the clot material is removed from the patient.

Several aspects of the present technology are set forth in the following additional examples:

1. A clot treatment system, comprising:
   an outer catheter defining a lumen;
   an inner catheter positioned at least partially in the lumen of the outer catheter; and a clot treatment device including a plurality of interconnected struts forming a unitary structure movable between a compressed configuration and an expanded configuration, wherein in the expanded configuration the unitary structure includes—
   a proximal connection region coupled to the outer catheter;
   a proximal conical region extending from the proximal connection region, wherein a first portion of the struts form first cells in the proximal conical region;
   a cylindrical region extending from the proximal conical region;
   a distal conical region extending from the cylindrical region, wherein a second portion of the struts from second cells in the distal conical region, and wherein the second cells are smaller than the first cells; and
   a distal connection region extending from the distal conical region and coupled to the inner catheter.

2. The clot treatment system of example 1 wherein the inner catheter has (a) a distal end portion coupled to the distal connection region of the clot treatment device and (b) a proximal end portion configured to float within the lumen of the outer catheter.

3. The clot treatment system of example 1 or example 2 wherein the inner and outer catheters are configured to receive a guidewire therethrough.

4. The clot treatment system of any one of examples 1-3, further comprising a handle coupled to a proximal end portion of the outer catheter, wherein the handle includes an actuation mechanism coupled to a proximal end portion of the inner catheter, and wherein actuation of the actuation mechanism is configured to translate the inner catheter relative to the outer catheter to longitudinally compress or longitudinally elongate the clot treatment device.

5. The clot treatment system of any one of examples 1-4, further comprising:
   a delivery catheter defining a lumen; and
   a handle coupled to a proximal end portion of the outer catheter and movable between a first position and a second position relative to the delivery catheter, wherein—
   in the first position, the clot treatment device is constrained within the lumen of the delivery catheter in the compressed configuration, and
   in the second position, the clot treatment device is positioned distal of the lumen in the expanded configuration.

6. The clot treatment system of example 5, further comprising a hub coupled to a proximal end portion of the delivery catheter, wherein the handle includes a lock feature configured to secure the handle to the hub in the second position.

7. The clot treatment system of example 5 or example 6 wherein the handle, the delivery catheter, the outer catheter, and the inner catheter are configured to receive a guidewire therethrough.

8. The clot treatment system of any one of examples 1-7 wherein, in the expanded configuration, the cylindrical region has a diameter of between about 0.71 inch to about 1.34 inches.

9. The clot treatment system of any one of examples 1-8 wherein the struts of the clot treatment device are configured to self-expand from the compressed configuration to the expanded configuration when unconstrained.

10. The clot treatment system of any one of examples 1-9 wherein the struts of the clot treatment device include a shape memory material.

11. The clot treatment system of any one of examples 1-10 wherein the unitary structure includes (a) a first number of the struts in the proximal conical region and (b) a second number of the struts in the distal conical region that is greater than the first number of struts.

12. A method of clot removal, the method comprising:
   positioning a distal portion of a guide catheter proximate to clot material within a blood vessel of a human patient;
   advancing a clot treatment device through the guide catheter to proximate the clot material;
   expanding the clot treatment within the blood vessel distal of the clot material, wherein the clot treatment device includes a plurality of interconnected struts forming a unitary structure having a proximal portion and a distal portion, wherein the struts form a plurality of first cells in the proximal portion and a plurality of second cells in the distal portion, and wherein the first cells are larger than the second cells;
   generating suction at the distal portion of the guide catheter; and
   proximally retracting the clot treatment device through the clot material.

13. The method of example 12 wherein advancing the clot treatment device through the guide catheter includes advancing the clot treatment device over a guidewire.

14. The method of example 12 or example 13 wherein the proximal portion of the unitary structure is coupled to an outer catheter extending at least partially through the guide catheter, and wherein the distal portion of the unitary structure is coupled to an inner catheter extending at least partially through the outer catheter.

15. The method of example 14 wherein advancing the clot treatment device through the guide catheter includes advancing the clot treatment device over a guidewire extending through the guide, outer, and inner catheters.

16. The method of any one of examples 12-15 wherein generating suction at the distal portion of the guide catheter includes generating suction, before proximally retracting the clot treatment device, to aspirate a first portion of the clot material into the guide catheter.

17. The method of example 16 wherein proximally retracting the clot treatment device includes proximally retracting the clot treatment device through a second portion of the clot material remaining in the blood vessel to capture the second portion of the clot material.

18. The method of any one of examples 12-17 wherein proximally retracting the clot treatment device through the clot material includes capturing at least a portion of the clot material, and wherein the method further comprises retracting the clot treatment device and the captured clot material into the guide catheter.

19. A clot treatment system, comprising:
an outer shaft defining a lumen;
an inner shaft positioned at least partially in the lumen of the outer shaft; and
a plurality of interconnected struts forming a unitary structure having a proximal portion and a distal portion, wherein the proximal portion is coupled to the outer shaft, wherein the distal portion is coupled to the inner shaft, and wherein the struts form a plurality of first cells in the proximal portion and a plurality of second cells in the distal portion, and wherein the first cells are larger than the second cells.

20. The clot treatment system of example 12 wherein the outer shaft and the inner shaft are configured to receive a guidewire therethrough.

21. A clot treatment device, comprising:
a plurality of interconnected struts forming a unitary structure movable between a compressed configuration and an expanded configuration, wherein in the expanded configuration the unitary structure includes—
a proximal connection region;
a proximal conical region extending from the proximal connection region, wherein a first portion of the struts form first cells in the proximal conical region;
a cylindrical region extending from the proximal conical region;
a distal conical region extending from the cylindrical region, wherein a second portion of the struts from second cells in the distal conical region, and wherein the second cells are smaller than the first cells; and
a distal connection region extending from the distal conical region.

22. The clot treatment device of example 21, further comprising:
a first shaft coupled to the proximal connection region and defining a lumen; and
a second shaft coupled to the distal connection region and extending at least partially through the lumen of the first shaft.

23. The clot treatment device of example 21 or example 22 wherein the second shaft has (a) a distal end portion coupled to the distal connection region and (b) a proximal end portion configured to float within the lumen of the first shaft.

24. The clot treatment device of any one of examples 21-23 wherein the struts are configured to self-expand from the compressed configuration to the expanded configuration when unconstrained.

25. The clot treatment device of any one of examples 21-24 wherein the struts are made from a shape memory material.

26. A clot treatment device, comprising:
a plurality of interconnected struts forming a unitary structure having a proximal portion and a distal portion, wherein the struts form a plurality of first cells in the proximal portion and a plurality of second cells in the distal portion, and wherein the first cells are larger than the second cells.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:
1. A method for the intravascular treatment of clot material from within a blood vessel of a human patient, the method comprising:
positioning a distal portion of an aspiration catheter proximate to the clot material within the blood vessel, wherein the aspiration catheter defines an aspiration lumen;
generating vacuum pressure within a barrel of a syringe and storing the vacuum pressure within the barrel;
applying the vacuum pressure to the aspiration lumen to aspirate at least a first portion of the clot material into the aspiration lumen by opening a valve fluidically coupled to the barrel and the aspiration lumen;
determining that a second portion of the clot material remains within the blood vessel;
advancing a clot treatment device having an expandable member through the aspiration lumen such that the clot treatment device is positioned at least partially distal to the second portion of the clot material;
expanding the expandable member of the clot treatment device within the blood vessel distal of the clot material, wherein the expandable member includes a plurality of interconnected struts forming a unitary structure having a proximal region and a distal region, wherein the struts form a plurality of first cells in the proximal region and a plurality of second cells in the distal region, and wherein the first cells are larger than the second cells; and proximally retracting the expandable member through the second portion of the clot material to capture and/or disrupt the second portion of the clot material.

2. The method of claim 1, further comprising, after proximally retracting the expandable member:

generating additional vacuum pressure with the barrel of the syringe;

applying the additional vacuum pressure to the aspiration lumen to aspirate a third portion of the clot material into the aspiration lumen.

3. The method of claim 1 wherein determining that the second portion of the clot material remains within the blood vessel includes determining that the clot material comprises chronic clot material.

4. The method of claim 1 wherein determining that the second portion of the clot material remains within the blood vessel includes determining that the clot material comprises organized clot material.

5. The method of claim 1 wherein advancing the clot treatment device through the aspiration catheter includes advancing the clot treatment device system over a guidewire.

6. The method of claim 1 wherein (a) opening of the valve fluidly connects the barrel of the syringe to the aspiration lumen and (b) closing of the valve fluidly disconnects the barrel of the syringe from the aspiration lumen.

7. The method of claim 6 wherein generating the vacuum pressure within the barrel of the syringe includes generating the vacuum pressure within the barrel while the valve is closed.

8. The method of claim 7 wherein the syringe is a vacuum-pressure locking syringe.

9. The method of claim 1 wherein the syringe is a vacuum-pressure locking syringe.

10. The method of claim 1 wherein expanding the expandable member of the clot treatment device includes expanding the expandable member to substantially a diameter of the blood vessel.

11. The method of claim 1 wherein the advancing the clot treatment device through the aspiration lumen includes advancing the clot treatment device such that the expandable member is positioned entirely distal to the second portion of the clot material.

12. The method of claim 1 wherein the proximal region of the clot expandable member has a tapered shape that increases in diameter in a direction toward the distal region of the expandable member.

13. The method of claim 12 wherein the distal region of the clot expandable member is generally cylindrical.

14. The method of claim 13 wherein expanding the clot treatment device includes expanding the expandable member at least partially radially away from a longitudinal axis of the expandable member, and wherein the wherein the unitary structure of the expandable member further comprises:

a proximal connection region extending proximally from the proximal region, wherein individual ones of the struts at the proximal connection region (a) extend generally parallel to the longitudinal axis, (b) are positioned circumferentially about the longitudinal axis, and (c) include a proximal terminus;

a distal conical region extending distally from distal region; and a distal connection region extending distally from the distal conical region, wherein individual ones of the struts at the distal connection region (a) extend generally parallel to the longitudinal axis, (b) are positioned circumferentially about the longitudinal axis, and (c) include a distal terminus.

15. The method of claim 14 wherein the struts at the proximal connection region are secured to a clot treatment catheter of the clot treatment device, and wherein the struts at the distal connection region are secured to a distal tip of the clot treatment device.

16. The method of claim 1 wherein the clot material comprises a pulmonary embolism.

17. The method of claim 1 wherein the clot material comprises a deep vein thrombosis.

18. A method for the intravascular treatment of chronic clot material from within a blood vessel of a human patient, the method comprising:

positioning a distal portion of an aspiration catheter proximate to the clot material within the blood vessel, wherein the aspiration catheter defines an aspiration lumen;

coupling a syringe to the aspiration lumen via a fluid control device, wherein (a) opening of the fluid control device fluidly connects the syringe to the aspiration lumen and (b) closing of the fluid control device fluidly disconnects the syringe from the aspiration lumen;

generating vacuum pressure with the syringe while the fluid control device is closed;

opening the fluid control device to apply the vacuum pressure to the aspiration lumen to aspirate a first portion of the chronic clot material into the aspiration lumen;

advancing a clot treatment device having an expandable member through the aspiration lumen such that the expandable member is positioned at least partially distal to a second portion of the clot material remaining within the blood vessel after the aspiration;

expanding the expandable member of the clot treatment device within the blood vessel distal of the clot material, wherein the expandable member includes a plurality of interconnected struts forming a unitary structure having a proximal region and a distal region, wherein the struts form a plurality of first cells in the proximal region and a plurality of second cells in the distal region, and wherein the first cells are larger than the second cells; and proximally retracting the expandable member through the second portion of the clot material to capture and/or disrupt the second portion of the clot material.

19. The method of claim 18, further comprising, after proximally retracting the expandable member:

generating additional vacuum pressure with the syringe while the fluid control device is closed; and opening the fluid control device to apply the additional vacuum pressure to the aspiration lumen to aspirate a third portion of the clot material remaining within the blood vessel after proximally retracting the expandable member into the aspiration lumen.

20. The method of claim 18 wherein expanding the expandable member of the clot treatment device includes expanding the expandable member to a diameter of the blood vessel, and wherein the distal region of the expandable member is generally cylindrical.

21. The method of claim 18 wherein the syringe is a vacuum-pressure locking syringe.

22. A method for the intravascular treatment of clot material from within a blood vessel of a human patient, the method comprising:
- positioning a distal portion of an aspiration catheter proximate to the clot material within the blood vessel, wherein the aspiration catheter defines an aspiration lumen;
- generating vacuum pressure within a barrel of a syringe and storing the vacuum pressure within the barrel;
- applying the vacuum pressure to the aspiration lumen to aspirate at least a first portion of the clot material into the aspiration lumen by opening a valve fluidically coupled to the barrel and the aspiration lumen;
- determining that a second portion of the clot material remains within the blood vessel;
- advancing a clot treatment device having an expandable member through the aspiration lumen such that the clot treatment device is positioned at least partially distal to the second portion of the clot material;
- expanding the expandable member of the clot treatment device within the blood vessel distal of the clot material, wherein the expandable member includes a plurality of interconnected struts forming a unitary structure having a conical region and cylindrical region distal of the conical region, wherein the struts form a plurality of first cells in the conical region and a plurality of second cells in the cylindrical region, and wherein the first cells are larger than the second cells; and
- proximally retracting the expandable member through the second portion of the clot material to capture and/or disrupt the second portion of the clot material.

* * * * *